United States Patent [19]

Williams et al.

[11] Patent Number: 4,818,752
[45] Date of Patent: * Apr. 4, 1989

[54] SOLUBLE PHOSPHORYLATED GLUCAN: METHODS AND COMPOSITIONS FOR TREATMENT OF NEOPLASTIC DISEASES

[75] Inventors: David L. Williams, River Ridge; I. William Browder, New Orleans, both of La.; Nicholas R. DiLuzio, deceased, late of New Orleans, La., by Nicholas M. DiLuzio, legal representative

[73] Assignee: Bioglucans, L.P., New Orleans, La.

[*] Notice: The portion of the term of this patent subsequent to Apr. 19, 2005 has been disclaimed.

[21] Appl. No.: 13,298

[22] Filed: Feb. 10, 1987

Related U.S. Application Data

[63] Continuation-in-part of Ser. No. 767,388, Aug. 19, 1985, Pat. No. 4,739,046.

[51] Int. Cl.$^4$ .................. A61K 31/66; C08B 37/00
[52] U.S. Cl. ..................................... 514/54; 536/117; 536/124
[58] Field of Search .................. 536/117, 124; 514/54

[56] References Cited

U.S. PATENT DOCUMENTS

| | | | |
|---|---|---|---|
| 3,081,226 | 3/1963 | DiLuzio | 514/61 |
| 3,396,082 | 8/1968 | Davis et al. | 536/1.1 |
| 4,138,479 | 2/1979 | Truschiet et al. | 424/88 |
| 4,202,966 | 5/1980 | Misaki et al. | 536/1.1 |
| 4,225,673 | 9/1980 | Sugiura et al. | 435/101 |
| 4,237,266 | 12/1980 | Sugiura et al. | 536/1 |
| 4,340,673 | 7/1982 | Stoudt et al. | 536/1.1 |
| 4,396,611 | 9/1983 | Ducon | 536/1.1 |
| 4,493,894 | 1/1985 | Miyashiro et al. | 435/101 |

OTHER PUBLICATIONS

Bärlin et al., in Heterogeneity of Mononuclear Phagocytes, Forster & Landy, eds., Academic Press, New York, pp. 243–252 (1981).
Chesterman et al., Toxicol. Lett. 9: 87–90 (1981).
Chirigos et al., Cancer Res. 39: 1085–1091 (1978).
Cozens et al., Toxicol. Lett 9: 55–64 (1981).
Deimann and Fahimi, J. Exper. Med. 149: 883–897 (1979).
DiLuzio and Riggi, J. Reticuloendothel. Soc. 8: 465–473 (1970).
DiLuzio, Trends in Pharmacol. Sci. 4: 344–347 (1983).
DiLuzio et al., Int'l J. Cancer 24: 773–779 (1979).
Ehrke et al., Int'l J. Immunopharm. 5: 34–42 (1983).
Glovsky et al., J. Reticuloendothel. Soc. 33: 401–413 (1983).
Hassid et al., J. Amer. Chem. Soc. 63: 295–298 (1941).
Holbrook et al., Am. J. Trop. Med. Hyg. 30: 762–768 (1981).
Liu et al., Life Sci. 29: 1027–1032 (1981).
Mansell and DiLuzio, in the Macrophage in Neoplasia, Fink, ed., Academic Press, New York pp. 227–243 (1976).
Niskanen et al., Cancer Res. 38: 1406–1409 (1978).
Patchen, Surv. Immunol. Res. 2: 237–242 (1983).
Patchen et al., J. Biol. Res. Mod. 3: 627–633 (1984).
Patchen and Lotzova Exper. Hematol. 8: 409–422 (1980).
Riggi and DiLuzio, Am. J. Physiol. 200: 297–300 (1961).

(List continued on next page.)

*Primary Examiner*—Ronald W. Griffin
*Attorney, Agent, or Firm*—Pennie & Edmonds

[57] ABSTRACT

A new class of soluble phosphorylated glucans is described as well as the process for making the same. According to one embodiment, the soluble phosphorylated glucan is derived from the yeast *Saccharomyces cerevisiae*. The soluble phosphorylated glucans are useful for prophylactic and therapeutic applications against neoplastic, bacteria, viral, fungal and parasitic diseases. The soluble phosphorylated glucans are used either alone or in combination with a known antimicrobial agent for prophylactic and therapeutic antimicrobial applications. Additionally, they may be administered either alone or as a non-toxic adjuvant, in combination with chemotherapy. The soluble phosphorylated glucans are also useful for stimulating macrophage cells, either in vivo or in vitro, to produce a cytotoxic/cyctostatic factor effective against cancer cells.

18 Claims, 5 Drawing Sheets

OTHER PUBLICATIONS

Saito, Carbohydrate Res. 58: 293–305 (1977).
Seljelid et al., Exper. Cell Res. 131: 121–129 (1981).
Schultz et al., in Immune Modulation and control of Neoplasia by Adjuvant Therapy, Chirigos, ed., Raven Press, New York pp. 241–248 (1978).
Suziuki et al., Gann 60: 273–277 (1969).
Williams et al., Hepatol. 5: 198–205 (1985).
Williams et al., Curr. Chemother. and Infectious Disease, Proc. 11th ICC and 19th ICAAC pp. 1724–1726 (1980).
Wooles and DiLuzio, Proc. Soc. Exper. biol. Med. 115: 756–759 (1964).
Yamamura and Azuma, Adv. Immunopharm. 2: 501–507 (1982).
Chihara, Rivista di Immunolog. ed. Immunofarm. 5(2):97–85 (1983).
Song and DiLuzio, in Lysosomes in Biology and Pathology, Dingle et al., eds., 6: 533–547 (1979).
Yosida et al., Adv. Pharmacol. Ther. II 6: 101–112 (1982).
DiLuzio and Williams, in Chemical Regulation of Immunology in Veterinary Medicine, Alan R. Liss, Inc., pp. 443–456 (1984), entitled "The Roll of Glucan in the Prevention and Modification of Microparasitic Diseases".
DiLuzio et al., in The Macrophage in Neoplasia; Academic Press, Inc. New York, pp. 181–198 (1976), entitled "The Employment of Glucan and Glucan Activated Macrophages in the Enhancement of Host Resistance to Malignancies in Experimental Animals".
DiLuzio and Chihara, in Advances in Immunopharmacology Hadden et al., eds., Pergamon press Oxford and New York, pp. 477–484 (1980).
Browder et al., Int. J. Immunopharmac. 6: 19–26 (1984), entitled "Modification of Post-Operative C. albicas Sepsis by Glucan Immunostimulation".
Jacques, in Current Concepts in Human Immunology and Cancer Immunomodulation, Serron et al., eds, Elsevier Biomedical Press BV, pp. 429–438 (1982), entitled "Immunomodulator Polysaccharides".
Mansell et al., in Immune Modulation and Control of Neoplasia by Adjuvant Chirigos eds., Raven Press, Inc., pp. 255–280 (1978).
Aoki, in Immunomodulating Agents: Properties and Mechanisms, Chirigos, eds, Marcel Dekker, 20:63–77 (1984).
Hamuro et al., in Immunomodulating Agents: Properties and Mechanisms, Chirigos, ed. Marcel Dekker, Inc., 20: 409–436 (1984).
Ashworth et al., Exper. Molec. Pathol. Supp. 1: 83–103 (1963), entitled "A Morphologic Study of the Effect of Reticuloendothealial Stimulation Upon Hepatic Removal of Minute Particles from the Blood of Rats".
Riggi and DiLuzio, Nature 193: 1292–1294 (1962), entitled "Hepatic Function during Reticuloendothelial Hyperfunction and Hyperplasia".
Wooles et al., Rad. Res. 16: 546–554 (1962) entitled "Influence of Pre- and post-X-Irradiation Zymosan Administration on Reticuloenothelial Function".
Bomford and Moreno, Br. J. Cancer 36: 41–48 (1977), entitled "Mechanisms of the Anti-Tumor Effect of Glucans and Fructosans: A Comparison with *C. Parrvum*".
Burgaleta and Golde, Cancer Res. 37: 1739–1742 (1977), entitled "Effect of Glucan on Granulopoiesis and Macrophage Genesis in Mice".
DiLuzio, in Kupffer Cells and Other Liver Sinusoidal Cells, Wisse and Knook eds., Elsevier Amsterdam, pp. 397–406 (1977).
DiLuzio et al., in The Macrophage and Cancer, James et al., eds., Edinburgh Univer. Med. Pres., pp. 181–201 (1977).
Schultz et al., Cancer Res. 37: 3338–3343 (1977), entitled "Association of Macrophage Activation with Anti--tumor Activity by Synthetic and Biologic Agents".
DiLuzio and Williams, Infection and Immun. 20: 804–810 (1978), entitled "Protective Effect of Glucan Against Systemic *Staphylococcus aureus* Septicemia in Normal and Leukemic Mice".
Wooles and DiLuzio, J. Reticuloendothelial. Soc. 1: 169–169 (1964); entitled "The Phagocytic and Proliferative Response of the Reticuloendothelial System Following Glucan Adminstration".
Browder et al., in Immunomodulation by Microbial Products and Related Synthetic Compounds, Yamamura et al., eds. Excerpta Medica, Amsterdam, pp. 354–357 (1982).
Cook et al., Infect. Immun. 37: 1261–1269 (1982) entitled "Protective Effect of Glucan Against Visceral Leishmaniasis in Hamsters".
Song and DiLuzio, in Lysosomes in Biology and Pa- (List continued on next page.)

OTHER PUBLICATIONS thology, Dingle et al., eds. North Holland Press Amsterdam 6: 533–547 (1979).

Popisil et al., Experientia 38: 1232–1234 (1982) entitled "Glucan Induced Enhancement of Hemopoietic Recovery in Gamma-Irradiated Mice".

Sasaki et al., J. Pharm. Dyn. 5: 1012–1016 (1982), entitled "Effect of Serum from Mice Treated with Antitumor Polysaccharide on Expression of Cytotoxicity by Mouse Peritoneal Macrophages".

Satoh et al., J. Pharm. Dyn. 5: 818–828 (1982), entitled "Elevation of Colony Stimulating Factors in Mouse Serum After Injection of PSK, an Antitumor Polysaccharide".

Jacques et al., in Sinusoidal Liver Cells, Knook et al., eds., Elsevier Biomedical Press, pp. 479–481 (1982).

DiLuzio et al., J. Reticuloendothelial Soc. 7: 731–742 (1970); entitled "Evaluation of the Mechanism of Glucan-Induced Stimulation of the Reticuloendothelial System".

Mansell et al., J. Nat'l Cancer Inst. 54: 571–580 (1975) entitled "Macrophage-Mediated Destruction of Human Malignant Cells in Vitro".

Inai et al., J. Immunol. 117: 1256–1260 (1976), entitled "Activation of the Alternative Complement Pathway By Water-Insoluble Glucans of *Streptococcus mutans*: the Relation Between Their Chemical Structures and Activating Potencies".

Proctor et al., J. Immunopharmacol. 3: 385–395 (1981–1982 entitled "Development of a Bioassay for Anti-Tumor Activity of Biological Response Modifers of the Reticuloendoethelial Stimulant Class: Reproducibility of the Bioassay".

Bogwald et al., Scand. J. Immuol. 15: 297–304 (1982) entitled "The Cytotoxic Effect of Mouse Macrophages Stimulated in vitro by a β1,3-D-Glucan from Yeast Cell Walls".

Williams et al., J. Reticuloendothel, Soc. 23: 479–490 (1978), entitled "Protective Effect of Glucan in Experimentally Induced Candidiasis".

Stewart et al., Cancer Treat. Prep. 62: 1867–1872 (1978), entitled "Preliminary Observations on the Effect of Glucan in Combination with Radiation and Chemotherapy in Four Murine Tumors".

Kohl et al., J. Immunol. Methods 29: 361–368 (1979) entitled "Inhibition of Human Monocyte-Macrophage and Lymphocyte Cytotoxicity to Herpes-simplex-infected Cells by Glucan".

Lahnborg et al., Eur. Surg. Res. 14: 401–408 (1982) entitled "Glucan-Induced Enhancement of Host Resistance in Experimental Intraabdominal Sepsis.

Lahnborg et al., J. Reticuloendothel. Cos. 32: 347–353 (1982) entitled "The Effect of Glucan-A Host Resistance Activator and Ampicillin on Experimental Intraabdominal Sepsis".

Kimura et al., J. Reticuloendothel. Soc. 34: 1–11 (1983), entitled "In Vitro Activation of Human Adherent Cells by a Glucan, Schizophyllan".

Mashiba et al., Japan J. Exp. Med. 53: 195–198 (1983), entitled "In Vitro Activation of Human Adherent Cells by a Glucan Schizophyllan".

Williams and DiLuzio, Science 208: 67–69 (1980), entitled "Glucan-Induced Modification of Murine Viral Hepatitis".

Proctor and Yamamura, J. Nat'l Cancer Inst. 61: 1179–1180 (1978); entitled "Letter to the Editor: Effectiveness of Glucan in the Treatment of Human Neoplasia".

Sasaki et al., Cancer Res. 38: 379–383 (1978), entitled "Dependence on Chain Length of Antitumor Activity of (1 3)-β-D-Glucan from *Alcaligenes faecalis* var. *myxogenes* IFO13140, and Its Acid-degraded Products".

DiLuzio and Williams, Cancer Immunol. Immunother. 6: 73–79 (1979), entitled "Glucan-Induced Modification of the Increased Susceptibility of Cyclophosphamide–Treated Mice to *Staphylococcus aureus* Infection.

Lotzova and Gutterman, J. Immunol. 123: 607–611 (1979), entitled "Effect of Glucan on Natural Killer (NK) Cells: Further Comparison Between NK Cell and Bone Marrow Effector Cell Activities".

Delville et al., Acta Leprologica 77/76: 273–281 (1979), entitled "Le-β1,3-Glucan et Autres Immunomodulateurs dans L'Infection lepresis Experimentale Chez La Souris".

Nuyen and Stadtsbaeder, in Advances in Exper. Med. and Biology, vol. 121A Escobar and Friedman, eds. Plenum Press, New York, pp. 255–266 (1980), entitled (List continued on next page.)

OTHER PUBLICATIONS

"Comparative Biological and Antitoxoplasmic Effects of Polysaccharides, In Vitro".

Gillet et al., in Advances in Exper. Med. and Biology, vol. 121A, Escobar and Friedman, eds., Plenum Press, New York, pp. 307–313 (1980), entitled "Particulate β1-3 Glucan and Casual Prophylaxis of Mouse Malaria (Plasmodium berghei)".

Leibovich et al., J. Reticuloendothel. Soc. 27: 1–11 (1980), entitled "Promotion of Wound Repair in Mice by Application of Glucan".

Cook et al., J. Reticuloendothel, Soc. 27: 567–573 (1980), entitled "Visceral Leishmaniasis in Mice: Protective Effect of Glucan".

Williams and DiLuzio, in the Reticuloendothelial System and Pathogenesis of Liver Disease Liehr and Grun. eds. Elsevier/North Holland Biomedical Press, pp. 363–368 (1980), entitled "Modification of Experimental Viral Hepatitis By Glucan Induced Macrophage Activation".

Browder et al., J. Surg. Res. 35: 474–479 (1983), entitled "Protective Effect of Nonspecific Immunostimulation in Post Splenectomy Sepsis".

Bogwald et al., J. Leucyte Biol. 35: 357–371 (1984), entitled "Lysosomal Glycosidase in Mouse Peritoneal Macrophages Stimulated In Vitro With Soluble and Insolubel Glycans".

Cook et al., Surv., Immunolog. Res. 2: 243–245 (1983), entitled "Immunomodulation of Protozoan Diseases".

Seljelid et al., Immunopharmacol. 7: 69–73 (1984), entitled "A Soluble β-1,3-D-Glucan Derivative Potentiates the Cytostatic and Cytolytic Capacity of Mouse Peritoneal Macrophages In Vitro".

Suga et al., Cancer Res. 44: 5132–5137 (1984), entitled "Antitumor Activity of Lentinan in Murine Syngeneic and Autochthonons Hosts and its Suppressive Effect on 3-Methylcholanthrene-induced Carcinogenesis".

Deslandes et al., Macromolecules 13: 1466–1471 (1980), entitled "Triple-Helical Structure (1 3)-β-D-Glucans".

Sarko et al., Biochem. Soc. Trans. 11: 139–142 (1983), entitled "Multiple-Helical Glucans".

Yanki et al., Biophys. Chem. 17: 337–342 (1983), entitled "Correlation Between the Antitumor Activity of a Polysaccharide Schizophyllan and its Triple-Helical Conformation in Dilute Aqueous Solution".

Sasaki et al., Cancer Treat. Rep. 67:275–280 (1983), entitled "Antitumor Activity of Tetrahydro-2-furanyl- -and tetrahydro-2-pyranyl-Glucans Obtained by Chemical Modification of (1 3)-βD-Glucan from Alcaligenes faecalis var. myxogenes IFO 13140 and its Lower Molecular Weight Glucans".

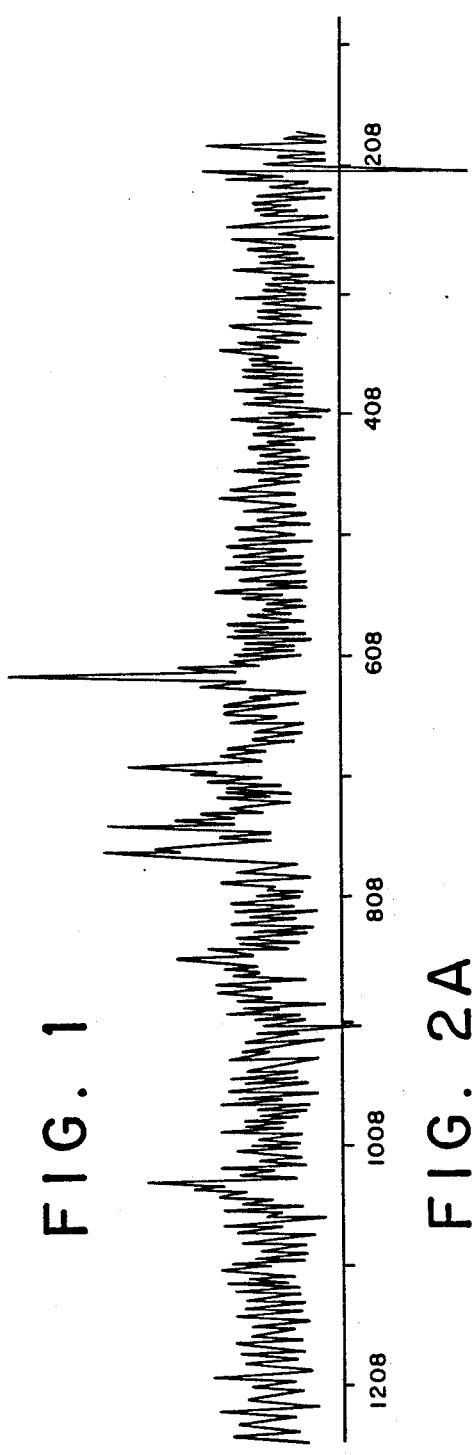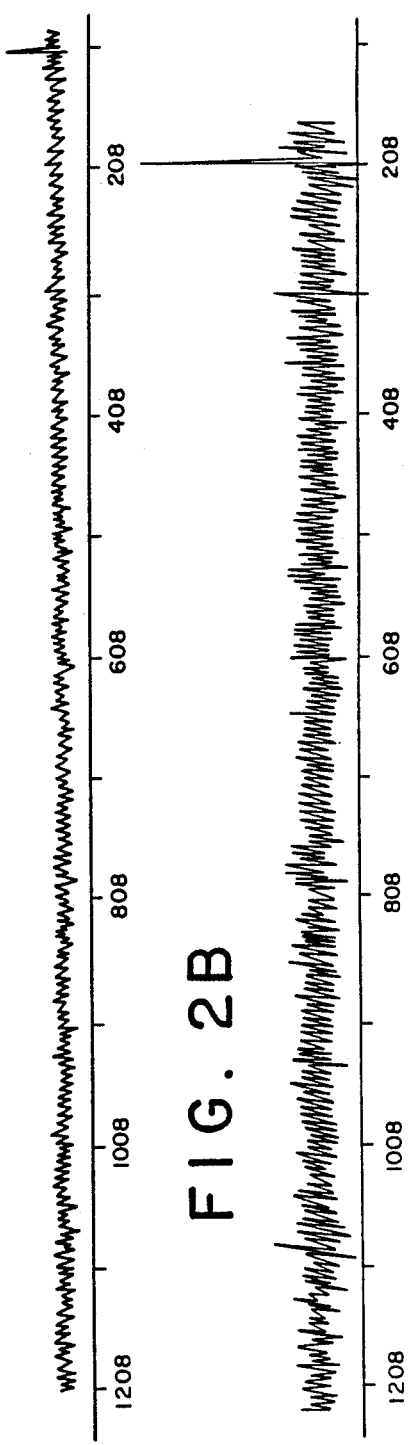
FIG. 1
FIG. 2A
FIG. 2B

○ = Cortisone  □ = Soluble Glucan
△ = Cortisone Plus  ○ = Glucose
    Soluble Glucan ○ = Cortisone  △ = Glucose
□ = Glucan  ○ = Cortisone Plus Glucan

SOLUBLE PHOSPHORYLATED GLUCAN: METHODS AND COMPOSITIONS FOR TREATMENT OF NEOPLASTIC DISEASES

CROSS REFERENCE TO RELATED APPLICATION

This application is a continuation-in-part application of copending Ser. No. 767,388 filed on Aug. 19, 1985, now U.S. Pat. No. 4,739,046, issued Apr. 19, 1988.

TABLE OF CONTENTS

1. Field of the Invention
2. Background of the Invention
    2.1. Immunobiological ctivity of Particulate Glucans
    2.2. Adverse Side Effects of Particulate Glucans
    2.3. Unsuccessful Attempts to Solubilize Particulate Glucans
3. Summary of the Invention
4. Brief Description of the Figures
5. Detailed Description of the Invention
    5.1. Process for Preparation of Soluble Phosphorylated Glucan
    5.2. Characterization of Soluble Phosphorylated Glucan
        5.2.1. Elemental Composition
        5.2.2. Structural Configuration
        5 2.2.1. Molecular Sieving
        5.2.2.2. Nuclear Magnetic Resonance Spectroscopy
    5.3. Non-toxicity, Non-pyrogenicity and Non-Immunogenicity of Soluble Phosphorylated Glucan
        5.3.1. Non-Toxicity
        5.3.2. Non-Pyrogenicity
        5.3.3. Non-Immunogenicity
    5.4. Uses of Soluble Phosphorylated Glucan
    5.5. Routes and Methods of Administration
6. Preparation of soluble Phosphorylated Glucans
    6.1. Preparation from Particulate Glucan Obtained from Saccharomyces
    6.2. Preparation from Coriolus versicolor
    6.3. Preparation from Sclerotium
7. Immunobiological Properties of Soluble Phosphorylated Glucans
    7.1. Modification of Enhanced Susceptibility to OpportunisticInfections in Immunosuppressed Animals
        7.1.1. Enhanced Survival
        7.1.2. Enhanced Resistance of Immuno-Suppressed Mice to *Escherichia coli* Infection
    7.2. Enhancement of Macrophage Phagocytic Activity
    7.3. Enhancement of Macrophage Secretory Activity
    7.4. Enhancement of Anti-Tumor Cytotoxin Production by Macrophages In Vitro
    7.5. Enhancement of Kupffer Cell Tumoricidal Activity
    7.6. Enhancement of Proliferation of Bone Marrow Cells In Vitro
    7.7. Enhancement of Splenocyte Response to Mitogens
    7.8. Modification of Metastatic Liver Disease
    7.9. Ability of Soluble Phosphorylated Glucan to Prevent Cyclophosphamide Induced Leukopenia
    7.10. Direct Cytostatic Effects on Neoplastic Cells
        7.10.1. Cytostatic Effect on Proliferation of Lymphocytic Leukemia Cells In Vitro
        7.10.2. Cytostatic Effect on Proliferation of Sarcoma and Melanoma Cells In Vitro

1. FIELD OF THE INVENTION

The present invention relates to pharmaceutical compositions and methods for therapeutic treatment of neoplastic diseases. More particularly, the invention relates to compositions and methods for treatment of a variety of neoplastic diseases using a novel class of soluble phosphorylated glucans in which the poly-[beta-(1-3)glucopyranose] chains are phosphorylated in varying degrees.

2. BACKGROUND OF THE INVENTION

The term "glucan" refers generically to a variety of naturally occurring homopolysaccharides or polyglucoses, including polymers such as cellulose, amylose, glycogen, laminarians, starch, etc. Glucan encompasses branched and unbranched chains of glucose units linked by 1-3, 1-4, and 1-6 glucosidic bonds that may be of either the alpha or beta type.

As defined herein, "particulate glucan" designates a water-insoluble particulate (about 1–3 microns) polyglucose such as that derived from the cell wall of the yeast *Saccharomyces cerevisiae*. Particulate glucan is macromolecular and comprises a closed chain of glucopyranose units united by a series of beta-1-3 glucosidic linkages. (Hassid et al., 1941, J. Amer. Chem. Soc. 63: 295–298; Di Luzio et al., 1979, Int'l J. Cancer 24: 773–779). X-ray diffraction studies have demonstrated that particulate glucans exist in the form of triple-stranded helices. (Sarko et al., 1983, Biochem. Soc. Trans. 11: 139–142).

2 1 IMMUNOBIOLOGICAL ACTIVITY OF PARTICULATE GLUCANS

Particulate glucan is a potent activator of the macrophage/monocyte cell series, complement, as well as of B cell lymphocytes. Thus, particulate glucan has profound effects on both the reticuloendothelial and immune systems.

Previous studies have demonstrated that in vivo administration of particuaate glucan to a variety of experimental animals induces a number of profound immunobiological responses, including the following: (1) enhanced proliferation of monocytes and macrophages (Deimann and Fahimi, 1979, J. Exper. Med. 149: 883–897; Ashworth et al., 1963, Exper. Molec. Pathol., Supp. 1: 83–103); (2) enhanced macrophage phagocytic function (Riggi and Di Luzio, 1961, Am. J. Physiol. 200: 297–300); (3) enhanced macrophage secretory activity (Bärlin et al., 1981, in Heterogeneity of Mononuclear Phagocytes, Forster and Landy, eds., Academic Press, New York, pp. 243–252); (4) increased macrophage size (Patchen and Lotzova, 1980, Exper. Hematol. 8: 409–422); (5) enhanced macrophage adherence and chemotactic activity (Niskanen et al., 1978, Cancer Res. 38: 1406–1409); and (6) enhanced complement activation (Glovsky et al., 1983, J. Reticuloendothel. Soc. 33: 401–413). Increased cytolytic activity against tumor cells has been demonstrated in macrophages from animals and man treated with particulate glucan both in vivo (Mansell and Di Luzio, 1976, in "The Macrophage in Neoplasia", Fink, ed., Academic Press, New York, pp. 227–243) and in vitro [Schultz et al., in Immune Modulation and Control of Neoplasia by Adjuvant Therapy, M.A. Chirigos, ed. Raven Press, New York, pp.241-48 (1978)].

Stimulation of the reticuloendothelial system by in vivo administration of particulate glucan leads to inhibition of allogenic or xenogenic bone marrow graft acceptance in lethally irradiated animals. (See, E. G. Wooles and Di Luzio, 1964, Proc. Soc. Exper. Biol. Med. 115: 756–759). This finding denotes that glucan will induce host defense mechanisms even against normal cells if they are genetically different from the host.

In addition to effects on reticuloendothelial and immune responses, in vivo administration of particulate glucan has been demonstrated to enhance hemopoietic activity including granulopoiesis, monocytopoiesis and erythropoiesis leading to greater recovery from a lethal dose of whole body irradiation (Patchen, 1983, Surv. Immunol. Res. 2: 237-242).

A number of studies have indicated that in vivo administration of particulaee glucan significantly modifies host resistance to a wide variety of infectious diseases induced by bacterial, fungal, viral and parasitic organisms. In particular, enhanced host resistance to infection has been shown when animals are challenged by microorganisms such as *Eshericheria coli, Staphylococcus aureus, Francisella tularensis, Mycobacterium leprae, Streptococcus pneumoniae, Candida albicans, Sporotrichum schenckii,* as well as viruses such as Venezuelan equine encephalomyelitis virus, Rift Valley fever virus, murine hepatitis virus, frog virus III, Herpes simplex I and II, and parasites such as *Leishmania donovani* (see review by Di Luzio, 1983, Trends in Pharmacol. Sci. 4: 344-347 and references cited therein).

Extensive studies have indicated that particulate glucan has potent anti-tumor activity. For example, particulate glucan has been shown to inhibit tumor growth and prolong survival in four syngeneic murine tumor models including adenocarcinoma BW 10232, anaplastic carcinoma 15091A, melanoma B16, and spontaneous lymphocytic leukemia BW5147 (Di Luzio et al, 1979, in Advances in Experimental Medicine and Biology, Vol. 121A: 269-290).

To evaluate the cellular basis of the anti-tumor activity of particulate glucan, the anti-tumor cytotoxic activity of peritoneal macrophages, derived from control and particulate glucan-treated mice, was studied (Mansell and Di Luzio, 1976, in The Macrophage in Neoplasia, Fink, ed. Academic Press, New York, pp. 227-243). These studies indicated that peritoneal macrophages from guucan-treated mice produced a significant cytotoxic response compared to normal macrophages. This observation has been confirmed (See, e.g., Bärlin et al. 1981,, in Heterogenity of Mononuclear Phagocytes, Forster and Landy, eds., Academic Press, New York, pp. 243-252) and Chirigos et al., 1978, Cancer Res. 38: 1085-1091).

Additionally in vitro studies using normal and tumor cells incubated with particulate glucan have demonstrated that glucan exerts a direct cytostatic effect on sarcoma and melanoma cells and a proliferative effect on normal spleen and bone marrow cells (Williams et al., 1985, Hepatology, 5: 198-206). These studies indicate that glucan, when administered therapeutically, will (1) significantly inhibit hepatic metastases; (2) inhibit the growth of the primary tumor; and (3) enhance survival, possibly by increased Kupffer cell tumoricidal activity as well as by a direct cytostatic effect of such glucan on sarcoma cells.

Notwithstanding these biological properties, the adverse side effects of particulate glucans have made these compounds all but useless in clinical medicine.

2.2 ADVERSE SIDE EFFECTS OF PARTICULATE GLUCANS

When particulate glucan is administered in vivo to animals, a number of severe side effects have become apparent, the most notable being:

(1) formation of granuloma;
(2) development of hepatosplenomegaly;
(3) increased susceptibility to endotoxins;
(4) activation of complement (anaphylyotoxin);
(5) development of pulmonary granulomatous vasculitis;
(6) development of hypotension following intravenous administration; and
(7) development of microembolism when administered at high concentrations.

Additionally, there is a relatively high degree of acute toxicity observed when particulate glucan is administered in vivo. For example, following a single intravenous injection of an aqueous suspension of particulate glucan, 20% and 100% morality were observed in mice receiving glucan at 250 and 500 mg/kg body weight respectively.

Moreover, due to the particulate nature of the glucan preparation (1–3 microns), it is difficult to administer via an intravenous route. By way of illustration, one patient receiving particulate glucan required constant supervision during intraveoous (IV) administration, continuous shaking of the IV drip bottle being essential to maintain the particulate glucan in suspension to avoid formation of emboli in the patient.

Although slightly soluble neutral glucans are commerically available, these preparations are not suitable for intravenous administration because the aqueous solutions have very high viscosity and, more importantly, because their use when administered to experimental animals has inevitably been accompanied by considerable toxicity.

Lentinan, a high molecular weight and poorly soluble beta-1,3 and beta-1,6 glucan obtained from *Lentinus edodes,* has been studied following intravenous administration to dogs. A variety of adverse clinical effects were observed following adminstration of lentinan (Ajinomoto Co. Inc., Tokyo, Japan) at doses of 2.0, 8.0 and 30 mg/kg/day for 5 weeks. Adverse effects included vomiting, erythema, discoloration of the sclera, and facial swelling. Circulatory collapse, unsteady gait, altered behavioral patterns, excessive salivation were also seen in individual beagles. At autopsy, congestion of the gastrointestinal mucosa was observed in animals treated with 2.0 or 8.0 mg/kg/day. Morphological changes of liver indicated intracytoplasmic material, possibly lentinan, accumulating in liver cells. One animal showed circulatory collapse upon the first injection at 8.0 mg/kg. While he did recover, the animal experienced repeated vomiting episodes with presence of blood indicating hemorrhaging of the gastrointestinal tract. Another animal appeared to show a marked allergic response, as demonstraed by erythema and subcutaneous swelling (edema) of the face. Autopsy findings demonstrated extensive edema of subcutaneous tissue, and congestion of the gastrointestinal tract with hemorrhaging. Macrophage cells showed accumulation of material, possibly lentinan. (Chesterman et al.,1981, Toxicol. Lett. 987-90)

Additional toxicity studies were performed in which a variety of doses of lentinan ranging from 0.1 to 1.0 mg/kg/da were given intravenously to rats for 9 weeks. Toxicity was manifested by the development of cutaneous lesions and discoloration of the ears suggesting thromboembolic events. (Cozens et al., 1981, Toxicol. Lett. 9: 55–64).

2.3. UNSUCCESSFUL ATTEMPTS TO SOLUBILIZE PARTICULATE GLUCANS

In view of these disadvantages of particulate beta-1,3 glucans for in vivo administration, extensive studies were undertaken to develop a soluble beta-1,3 polyglucose which might be non toxic, induce no significant pathology and yet retain significant immunobiological activity.

A low molecular weight non-phosphorylated soluble glucan preparation prepared by formic acid hydroylsis of particulate glucan has been shown to have anti-tumor and anti-staphylococcal activity (Di Luzio et al., 1979, Internat'l J. Cancer 24: 7737–779). Unfortunately, the low yield and diversity of fractions obtained by this method made this preparation non-useful for prophylactic and therapeutic applications. (see Di Luzio, 1983, Trends in Pharmacological Sciences 4: 344–347).

Similarly, attempts to solubilize particulate glucan by the addition of dimethylsulfoxide (DMSO) a "molecular relaxant" were also unsuccessful. It was thought the DMSO would "relax" the triple helical configuration of the glucan molecule. However, particulate glucan did not dissolve in the presence of DMSO. All attempts to isolate a soluble glucan from the DMSO solution resulted in failure. Upon dilution of the DMSO-glucan solution with various aqueous media suhh as glucose or saline solutions, the particulate glucan was reformed. Following dilution of the DMSO-soluble glucan solution with saline, all animals receiving injections of these solutions died immediately upon injection due to high concentration of DMSO or the reformation of the particulate glucan. Upon precipitation of the glucan in DMSO solution by the additon of ethanol (100%), the precipitate was collected and lyophilized. When this lyophilized glucan was added to water, the particulate glucan reformed.

Attempts to convert the neutral glucan preparation of particulate glucan to a polar-charged preparation by the addition of phosphate or sulfate groups as well as by acetylation were also unsuccessful. Each of these procedures was conducted following the attempted solubilization of particulate glucan by DMSO and in each instance the particulate glucan was reformed.

3. SUMMARY OF THE INVENTION

During an exhaustive investigation of methods by which the triple-stranded helices of glucan might be "relaxed" sufficiently to permit reaction of each of the chains, it was found that when particulate glucan was dissolved in a highly polar solvent (such as DMSO) in the presence of a strong chaotropic agent (such as urea), the glucan is sufficiently structurally disrupted to allow phosphorylation of each of the single chains (or strands) such that the resultant phosphorylated glucan shows the substantially complete absence of the characteristic triple helica structure of particulate glucan. Removal of the resultant phosphorylated glucan shows it to be soluble in water, non-toxic, non-immunogenic, substantially non-pyrogenic and capable of exerting profound immunobiological responses when administered in vivo to animals and humans.

Based on these discoveries, the invention provides a new class of soluble phosphorylated glucans (a) in which the poly-[beta-(1-3)glucopryanose] chains are phosphorylated in varying degrees; (b) which are non-toxic, non-immunogenic, substantially non-pyrogenic, and (c) which are capable of exerting pronounced immunobiological responses when administered in vivo in animals and humans. These new soluble phopsphorylated glucans, which are further characterized by a substantial absence of the triple helical structure of particulate glucans, immunostimulate macrophage activity with resulting activation of other immunoactive cells in the reticuloendothelial and immune systems. Additionally these soluble phosphorylated glucans enhance hemopoietic activity including but not limited to leukopoiesis. These soluble phosphorylated glucans exhibit cytostatic effects against adenocarcinomas and sarcomas in vivo, and against lymphocytic leukemia cells in vitro. Not only do these soluble phosphorylated glucans stimulate macrophage cells in vivo, but they exert profound stimulatory effects on macrophage cells cultured in vitro. Such immunostimulttion of macrophage cells is invariably accompanied by production of a macrophage cytotoxic/cytostatic factor (MCF), protein or proteins of unknown structure, which are selectively toxic to cancers cells, particularly adenocarcinomas.

Additionally, the invention provides a process for producing these soluble phosphorylated glucans by dissolving a particulate glucan (preferably prepared from Saccharomyces cerevisiae although other microbial sources may be used) in a highly polar solvent which contains a strong chaotropic agent, and reacting the resultant glucan with phosphoric acid to form a soluble phosphorylated glucan, and recovering the resultant phosphorylated glucans from the reaction mixture.

Further, the present invention provides methods and compositions for treatment of malignant neoplastic disease in animals and humans which comprise administering to an animal or a human a therapeutically effective amount of a soluble phosphorylated glucan alone or in combination with an anti-cancer or anti-tumor agent. The invention also provides methods and compositions for prevention of leukopenia induced by administration of an anti-cancer agent which comprise administering to an animal or a human, an effective amount of soluble phosphorylated glucan in combination with said anti-cancer agent.

Furthermore, the invention provides methods for stimulating animal and human macrophage cells (in vivo or in vitro) to produce and secrete a soluble cytotoxic/cytostatic factor (MCF) and the product so produced. Specifically, MCF is produced by administering to an animal or a human a soluble phosphorylated glucan or by culturing animal or human macrophage cells in vitro in culture medium containing soluble phosphorylated glucan.

The immunobiological properties of the soluble phosphorylated glucans of the invention include (1) the ability to prevent mortality due to overwhelming gram negative bacterial infections; (2) the ability to prevent mortality due to gram positive bacterial infections; (3) the ability to modify mortality from spontaneous infections in profoundly immuno-suppressed animals and man; (4) the ability to modify enhanced susceptibility of immunosuppressed animals and man to gram negative bacterial infections; (5) the ability to significantly modify viral infections; (6) the ability to modify spontaneous infections induced by fungal and other parasitic microorganisms; (7) the ability to significantly inhibit primary tumor growth when used alone and to exert a synergistic effect against primary tumor growth when used in combination with anti-cancer agents; (8) the ability to act synergistically with anti-cancer agents in the regression of primary malignant lesions as well as metastatic lesions in animals and man.

Because of these unique immunobiological properties, soluble phosphorylated glucan is particularly useful for therapeutic applications against a variety of neoplastic conditions as well as against a variety of diseases induced by bacteria, viruses, fungi and parasitic organisms. Soluble phosphorylated glucan is advantageously administered either alone, with a physiologically acceptable pharmaceutical carrier or in combination with another bioactive or pharmacological agent and with another therapeutic modality such as chemotherapy or surgery.

4. BRIEF DESCRIPTION OF THE FIGURES

The present invention may be more fully understood by reference to the following detailed description of the invention, examples of specific embodiments and the appended figures in which:

FIG. 1 is a representation of the nuclear magnetic resonance spectrum of soluble phosphorylated glucan at 27 mg/ml.

FIG. 2 is representation of the nuclear magnetic resonance spectrum of a commercially available preparation of lentinan (Ajinomoto co. Inc., Tokyo, Japan). FIG. 2A is an illustration of the spectrum obtained at a concentration of 40 mg/ml. FIG. 2B is an illustration of the spectrum obtained at a concentration of 3 mg/ml lentinan.

FIG. 3 also illustrates the effect of chronic administration of soluble phosphorylated glucan on survival of normal mice.

Figure 7:
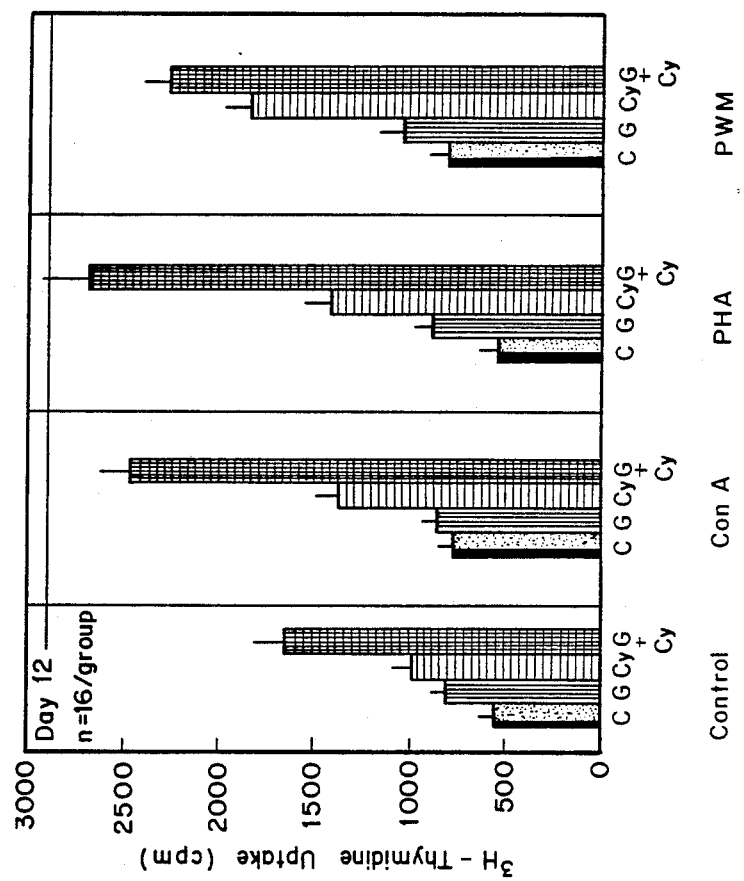

FIG. 7 is a graphical illustration of splenocyte proliferation and response to mitogens observed in splenocytes obtained from animals treated with soluble phosphorylated glucan, cyclophosphamide or soluble phosphorylated glucan and cyclophosphamide. Mitogens represented are: concanavalin A (ConA), phytohemagglutinin (PHA) and pokeweed mitogen (PWM). Cells in RPM1 1640 medium served as controls (Control).

5. DETAILED DESCRIPTION OF THE INVENTION

Aqueous soluble phosphorylated glucan represents a novel class of soluble phosphorylated glucans in which the poly-[beta-(1-3)glucopyranose] chains are phosphorylated in varying degrees. Soluble phosphorylated glucan shows the substantially complete absence of the characteristic triple helical structure of particulate glucan. Because soluble phosphorylated glucan stimulates macrophage phagocytic and secretory activity and increases proliferation of macrophages, it is advantageously used to treat malignant neoplastic diseases, including but not limited to adenocarcinoma, reticulum cell sarcoma, lymphocytic leukemia, melanoma, etc. The soluble phosphorylated glucan is advantageously used either alone or in combination with another bioactive or pharmacological agent or therapeutic modality such as chemotherapy and surgery.

Because of the potent activity of the soluble phosphorylated glucan in stimulating the immune response and reticuloendothelial system, it is also particularly useful for prophylactic and therapeutic applications against a variety of diseases induced by bacteria, viruses, fungi, and parasitic organisms. Copending application of Williams, Browder and DiLuzio, Ser. No. 130082, filed on even date herewith is directed specifically to compositions and methods for these applications and is incorporated herein by reference.

5.1. PROCESS FOR PREPARATION OF SOLUBLE PHOSPHORYLATED GLUCAN

Aqueous soluble phosphorylated glucan is prepared by a process which results in a unique class of products different from any other glucans previously described.

Soluble phosphorylated glucan is prepared from particulate glucan, a neutral polyglucose deiived, for example from *Saccharomyces cerevisiae*, as follows: particulate glucan is suspended in a solution of a strong chaotropic agent in an aprotic solvent such as dimethylsulfoxide (DMSO) with constant stirring. The strong chaotropic agent "relaxes" hydrogen bonding along the polyglucose chain, thus unfolding the molecule. It is preferred to use a fairly high concentration of a strong chaotropic agent such as urea ranging from about 4-12M to prevent reformation of hydrogen bonds. The mixture is then heated and maintained at about 50°-150° C. and phosphoric acid is slowly added with constant stirring. A precipitate comprising the soluble phosphorylated glucan product is apparent after about 1 hour. It is preferred to maintain the reaction mixture at about 100° C. for about 3-12 hours to increase the yield of bioactive product. In practice, after reaction for about 6 hours at about 100° C., the yield is approximately 70-90%. The degree of phosphorylation of the soluble product varies slightly with reaction time (e.g., 1.48% for 3 hours; 2.23% for 6 hours).

The bioactive soluble phosphorylated glucan product is isolated from the reaction mixture as follows: the mixture is cooled to stop the phosphorylation reaction and diluted with a volume of distilled water sufficient to resuspend the precipitate. The resulting solution is filtered through coarse, medium and fine sintered funnels to remove any remaining precipitate. The solution is then molecularly sieved to remove all components of less than about 10,000 daltons molecular weight (MW). Thus, DMSO, urea, glucose and any unreacted phosphoric acid are removed from the solution. Molecular sieving may be accomplished by any method that removes these low (i.e., less than about 10,000 daltons) MW components. In one illustrative example, the solution is sieved using Spectrapor membrane dialysis tubing and dialyzing against running distilled water for about 5 days. In another illustrative example, the solution is sieved using a Millipore dialyzer/concentrator with a 10,000 dalton MW membrane filter and a large volume of dialyzing solution. Following molecular sieving, the resulting solution is concentrated and lyophilized to yield the final soluble phosphorylated glucan in the form of a fluffy powder composition. Crystalline structures are not observed.

The particulate glucan used in the process for preparing the soluble phosphorylated glucan according to the present invention may be isolated from the cell wall of *S. cerevisiae* by known methods (see e.g., Di Luzio et al., 1979, Internat'l J. Cancer224: 773-779; Hassid et al., 1941, J. Amer. Chem. Soc. 63: 295-298 incorporated herein by reference). Briefly, in practice the particulate glucan is prepared as follows: dry yeast is digested in aqueous sodium hydroxide solution and heated to about 100° C. for about 4 hours, then allowed to settle overnight. The supernatant is decanted and the procedure is repeated three times. The residue is acidified using hydrochloric acid, heated to and maintained at 100° C. for about 4 hours, and cooled overnight. The supernatant is decanted and the acid digestion is repeated twice. The residue is then washed repeatedly with distilled water and extracted with ethanol for at least 24 hours. The reddish-brown supernatant is then aspirated and discarded. The ethanol extraction is repeated until the supernatant is essentially colorless. The ethanol is removed by repeatedly washing the residue with distilled water. The particulate glucan is collected by centrifugation or filtration.

A variety of compounds, other than urea, known to function as "molecular relaxants" were also evaluated to prevent reformation of hydrogen bonds after DMSO had been used to "relax" the triple helical configuration of particulate glucan. These include (1) ethylene diamine tetracetic acid; (2) hydrazine sulfate; (3) monoethanol amine; (4) guanidine; (5) guanine, and (6) thiourea. Additionally, surfactants and emulsifying agents such as Tween-20 and phospholipid emulsifying agents such as Alcolec and Centrolex f (lecithin) were also employed in an attempt to solubilize and phoshorylate particulate glucan. In no case was a soluble immunobiologically active preparation obtained.

Additionally, soluble phosphorylated glucan can be prepared from neutral polyglucose or polyglucose-protein products derived from a variety of other microbial sources. A non-exhaustive list of such sources is presented in Table 1.

TABLE 1

EXAMPLES OF SOURCES OF GLUCAN WHICH CAN BE EMPLOYED FOR THE PREPARATION OF SOLUBLE PHOSPHORYLATED GLUCAN

Alcaligenes faecalis
Auricularia auricula-judae
Auricularia polytricha
Candida utilis
Cladosporium fulvum
Claviceps purpurea
Cochiliobolus sativus
Coriolus versicolor
Corlinellus shiitake
Corticium vagum
Grifola umbellata
Lentinus edodes
Pichia fermentans
Poia cocos
Saccharomyces cerevisiae
Sclerotium coffeicolum
Sclerotium delphnii
Sclerotium glucanium
Sclerotium rolsfi
Shizophyllum commune
Streptococcus salvarius
Stereum sanguinolentum
Wingea robertsii According to another alternate embodiment of the present invention, the soluble phosphorylated glucan may be obtained from the medium used to culture an organism such as *Sclerotium glucanium* using a novel, rapid process. Briefly in practice, a colloidal glucan is prepared from *Sclerotium glucanium* as follows:

A crude sclero-glucan, comprising a polyglucose chain of linearly arrange glucose units linked by beta 1-3 glucosidic bonds in which about 30-35% of the linear chains have a single glucose unit attached via a beta 1-6 bond obtained from the medium used to culture *Sclerotium glucanium*, is mixed slowly with aqueous sodium hydroxide solution with heat and constant stirring. The mixture is allowed to stand at room temperature for about 4 days, heated to about 50°-100° C. for about 15-60 minutes and then the mixture is allowed to cool to room temperature. The colloidal glucan is isolated from the mixture either by centrifugation or filtration. To illustrate, when filtration is used a series of filters of decreasing pore size such as 3.0, 1.2, 0.8, 0.65 microns are used. The resulting dark amber filtrate is diluted with water and molecularly sieved to removed all components of less than about 10,000 daltons molecular weight. In one illustrative example, the mixture is sieved using spectropor membrane dialysis tubing and dialyzing against 40 liters of water. The final concentrated mixture having about neutral pH is lyophilized yielding an amber spongy glucan material. In another illustrative example, the mixture is dialyzed and concentrated using a Pellicon dialyzing unit. The mixture is dialyzed against 75 liters of pure water. The final concentrated mixture having about neutral pH is lyophilized yielding an amber spongy colloidal glucan material.

Soluble phosphorylated glucan is prepared from the colloidal glucan as described above. Briefly, colloidal glucan is suspended in a solution of a strong chaotropic agent in an aprotic solvent such as dimethylsulfoxide (DMSO) with constant stirring. The strong chaotropic agent "relaxes" hydrogen bonding along the polyglucose chain, thus unfolding the molecule. It is preferred to use a fairly high concentration of a strong chaotropic agent such as urea ranging from about 4-12M to prevent reformation of hydoogen bonds. The mixture is then heated and maintained at about 50°-150° C. and phosphoric acid is slowly added with constant stirring. A precipitate comprising the soluble phosphorylated glucan product is apparent after about 1 hour. It is preferred to maintain the reaction mixture at about 100° C. for about 3-12 hours to increase the yield of bioactive product. In practice, after reaction for about 6 hours at about 100° C., the yield is approximately 70-90%. The degree of phosphorylation of the soluble product varies slightly with reaction time (e.g., 1.48% for 3 hours; 2.23% for 6 hours).

5.2. CHARACTERIZATION OF SOLUBLE PHOSPHORYLATED GLUCAN

The solubility of the soluble phosphorylated glucan obtained from *S. cerevisiae* prepared according to the present invention is greater than about 50 mg/ml in water. Aqueous solutions of the soluble phosphorylated glucan are non-viscous and do not taste sweet.

5.2.1. ELEMENTAL COMPOSITION

The elemental composition of the soluble glucan preparation, determined by Galbraith Laboratories, (Knoxville, Tenn.) is illustrated in Table 2. The data presented in Table 2 permits the average empirical formula of this preparation to be writtnn as follows:

$$C_{40}H_{87}PO_{37}.$$

Thus, there is an average of one phosphate group for every 6.6 glucose residues in the soluble phosphorylated glucan.

TABLE 2

| ELEMENTAL COMPOSITION OF SOLUBLE PHOSPHORYLATED GLUCAN[a] | |
|---|---|
| Element or Component | Mole % |
| Carbon | 34.66 |
| Hydrogen | 6.29 |
| Oxygen | 42.83 |
| Nitrogen | 0.64 |
| Sulfur | 0.11 |
| Phosphorus | 2.23 |
| Water of Hydration | 11.78 |

[a]Determined after 6 hours phosphorylation.

5.2.2. STRUCTURAL CONFIGURATION

A number of methods were utilized to determine the molecular weight (MW) and various features of the structural configuration of the soluble phosphorylated glucan.

5.2.2.1. MOLECULAR SIEVING

Column chromatography using Sepharose CL-6B-200 (Pharmacia Fine Chemicals, Piscataway, N.J.) indicated that 80% of the soluble glucan has a MW range from 10,000 to 100,000 daltons, while 20% has a MW range from about 100,000 to about 500,000 daltons.

5 2 2.2. NUCLEAR MAGNETIC RESONANCE SPECTROSCOPY

Carbon-13 nuclear magnetic resonance ($^{13}$C-NMR) spectroscopy using a Brucker WP-200 spectrometer (Brucker Instruments, Billerica, Mass.) was performed to determine several structural properties of the soluble phosphorylated glucan from *S. cervisiae* prepared according to the present invention.

The samples for NMR studies were prepared using a 10% deuterium oxide ($D_2O$) in water. Samples were first run with no reference material, and then after the addition of a small aliquot of 1,4-dioxane. All samples were placed in 10 mm diameter tubes.

The $^{13}$C-NMR spectral study of soluble phosphorylated glucan indicated a beta-1-3 glucan structure with no branching at the C-6 carbon (see FIG. 1). The NMR spectrum indicates a substantial absence of the triple helical structure of particulate glucans. The degree of phosphorylation was estimated to be 3.6% which is in essential accord with analytical data.

In contrast to the spectra of soluble phosphorylated glucan from *S. cerevisiae* prepared according to the present invention, a lentinan preparation (Ajinomoto Co. Inc., Tokyo Japan), a branched beta-1-3 and 1-6 D glucan, at either 40 mg/ml (FIG. 2A) or 3 mg/ml (FIG. 2B) demonstrated attenuation of the NMR spectra. This is presumed to be due to the gel state of this molecule, particularly at 40 mg/ml concentration. No signals were obtained in a 10% $D_2O$ solution in the non-gel 3 mg/ml concentration.

Comparison of FIG. 1 with FIG. 2 demonstrates complete structural and conformational differences between lentinan and soluble phosphorylated glucan. In contrast to the disordered conformation of lentinan at the beta-1-6 linkages (Saito et al., 1977, Carbohydrate Research, 58: 293–305) ordered conformation of soluble phosphorylated glucan according to the present invention is manifested.

5.3. NON-TOXICITY, NON-PYROGENICITY NON-IMMUNOGENICITY OF SOLUBLE PHOSPHORYLATED GLUCAN

Since the soluble phosphorylated glucan offers important advantages over particulate glucan as an injectable biological response modulator, characteristic toxicity, pyrogenicity and immunogenicity of the soluble glucan are described below with particular reference to comparison of these properties of particulate glucan.

5.3.1 NON-TOXICITY

Acute toxicity as evaluated following a single intravenous injection of soluble phosphorylated glucan at a variety of doses into normal animals. Treated animals were observed for 30 days post-injection.

In one series of experiments, 49 ICR/HSD mice were divided into 3 groups of 15 mice each and 2 groups of 2 mice each. Groups 1–3 received 0.5 ml saline solution containing soluble phosphorylated glucan at respectively 40, 200 and 1000 mg/kg; Groups 4 and 5, 1600 and 2000 mg/kg. No mortality was observed in any group. Moreover, no physiological or behavioral alterations were apparent. In marked contrast, in mice treated similarly with particulate glucan, 20% mortality was observed at 250 mg/kg and 100% mortality at 500 mg/kg.

In another series of experiments, two groups of 5 Sprague Dawley rats each were treated with soluble phosphorylated glucan at respectively 250 and 500 mg/kg via intravenous injection. No mortality or alteration of physiological or behavioral functions was apparent in either group. In contrast, 30% and 100% mortality were observed following intravenous injection of particulate glucan at 75 and 150 mg/kg respectively.

Chronic toxicity was evaluated following twice weekly intravenous injections of saline solution containing soluble phosphorylated glucan at 0, 40, 200 and 1000 mg/kg doses. Body and organ weights, gross and microscopic pathology, serum electrolytes, solutes and serum enzymes indicative of renal and hepatic function were monitored.

In one series of experiments mice were weighed respectively at 0, 8, 11, 15, 22 and 30 days post-treatment With soluble phosphorylated glucan. No significant difference was observed in body weight at any dose of soluble phosphorylated glucan administered. After 30 days chronic treatment, animals were sacrificed. No change was seen in weight of liver, lung and kidney. A statistically significant increase in spleen weight was noted in mice treated with 40 and 100 mg/kg soluble glucan ($0.01 < p < 0.001$), but not in mice treated with 200 mg/kg.

In another series of experiments, mice were weighed respectively at 0, 15, 30, 49 and 60 days post-treatment (twice weekly) with soluble phosphorylated glucan. No significant difference was observed in body weight at any dose of soluble phosphorylated glucan administered. After 60 days chronic treatment with soluble phosphorylated glucan, animals were sacrificed. No significant difference was observed in weight of the liver, kidney or lung. A statistically significant increase in spleen weight was apparent in mice treated with 1000 mg/kg soluble phosphorylated glucan ($p < 0.001$).

After 30 or 60 days chronic treatment, no significant alteration was apparent in the following serum components: glucose, blood urea nitiogen (BUN), uric acid, cholesterol, triglycerides, total protein, albumin, globulin, creatinine, calcium, phosphorous, sodium, potassium, chloride, bicarbonate and anion gap. Moreover, no significant alteration was apparent in the following enzymes: alkaline phosphatase, lactic dehydrogenase, serum glutamic oxalacetic transaminase, serum glutamic pyruvic transaminase and creatinine phosphokinase. No change was detectable in serum bilirubin.

Histological studies on tissues obtained from mice following 30 days chronic treatment showed essentially normal liver histology in mice receiving 40 and 200 mg/kg soluble phosphorylated glucan per injection. In animals receiving 1000 mg/kg soluble phosphorylated glucan, monocytic infiltrates were readily apparent in the liver. Lung and kidney tissues were essentially normal in all mice.

Histological studies on tissues obtained from mice following 60 days chronic treatment showed few hepatic granuloma of an isolated nature in animals receiving injections at 40 and 200 mg/kg doses. A higher number of monocytic infiltrates was observed in mice receiving injections at 1000 mg/kg. In all autopsied animals, lung tissue was essentially normal.

Chronic toxicity was further evaluated using guinea pigs (Harlan Sprague Dawley, Houston, Tex.) receiving 5 ml intraperitoneal injections of saline solution containing soluble phosphorylated glucan at 250 mg/kg for 7 days (FDA required test). Results presented in Table 3 indicate that there was an impairment of growth of guinea pigs receiving soluble glucan treatment when compared to controls receiving an equivalent volume of 0.9% saline solution. Following 7 days chronic treatment, body weight of treated animals was, however, significantly increased by 9% as compared to initial weight.

Chronic Toxicity was also evaluated in 2 adult female dogs receiving twice weekly intravenous administration (5 mg/kg) of soluble phosphorylated glucan for 120 days. The dogs were fed Purina Chow and water ad libitum supplemented with one can commercial dog food (Alpo TM) twice weekly. Body weight and serum solutes, electrolytes and enzymes were monitored at 0, 17, 24, 38, 80 and 120 days. Following 120 days chronic treatment, a mean weight gain of 2.8 kg or about 22% body weight was observed.

No significant difference was observed in the following serum solutes: glucose, BUN, uric acid, cholesterol, triglycerides, total protein, albumin, globulin, or creatinine. No significant difference was observed in the following serum electrolytes: calcium, phosphorous, sodium, potassium, chloride, bicarbonate, and anion gap. No significant difference was observed in the following serum enzymes: alkaline phosphatase, lactic dehydrogenase, serum glutamic oxalacetic transaminase, serum glutamic pyruvic transaminase and creatinine phosphokinase.

Additionally, no significant difference has been observed in the serum biochemistry of a patient following therapy for 3 months with soluble phosphorylated glucan at 50 mg/ml, administered three times per week.

5.3.2. NON-PYROGENICITY

Pyrogenicity of soluble phosphorylated glucan was evaluated following a single intravenous injection to conscious dogs at doses of 7.5 mg/kg and 30 mg/kg. Body temperature was monitored for 14 days post-injection.

Results presetted in Table 4, demonstrate no pyrogenic reaction in this chronic animal model.

TABLE 4

| ABSENCE OF AN ACUTE OR CHRONIC PYROGENIC RESPONSE IN DOGS | | | | | | |
|---|---|---|---|---|---|---|
| Treatment Dose[a] (mg/kg) | Mean Body Temperature (°C.) Time (Hours) | | | | | |
| | 0 | 1 | 6 | 24 | 144 | 336 |
| 7.5 | 38.3 | 37.4 | 38.3 | 38.3 | 38.3 | 38.4 |
| 30.0 | 38.6 | 37.0 | 38.0 | 38.5 | 38.4 | 38.6 |

[a]N = 3 dogs/group.

Pyrogenicity was also evaluated using three dogs anesthetized with Nembutal (30 mg/kg) receiving multiple injections of increasing doses of 1, 5, 10, 15, 25 and 50 mg/kg of soluble phosphorylated glucan over a three hour period. Body temperature was determined at 15 minutes following bolus injections. No pyrogenic effect was observed at any dose.

Pyrogenicity of soluble phosphorylated glucan was also evaluated in rabbits. Seven rabbits were divided into 2 groups of 2 and 5 rabbits each. Group 1 received an isovolumetric saline solution; Group 2, received 5 mg/kg soluble phosphorylated glucan in saline solution by intravenous injection. Core body temperature was monitored at 15 minute intervals for 100 minutes fol-

TABLE 3

| EFFECT OF CHRONIC ADMINISTRATION OF SOLUBLE PHOSPHORYLATED GLUCAN ON BODY WEIGHT | | | | | | | |
|---|---|---|---|---|---|---|---|
| Treatment | Mean Body Weight (gm)[a] Days | | | | | | |
| | 1 | 2 | 3 | 4 | 5 | 6 | 7 |
| Saline | 213.8 ± 4.0 | 225.2 ± 6.6 | 227.4 ± 7.1 | 234.2 ± 7.3 | 239.7 ± 6.1 | 244.2 ± 5.2 | 253.8 ± 7.5 |
| SPGLN[b] | 208.9 ± 2.9 | 202.3 ± 5.0 | 203.9 ± 5.3 | 207.4 ± 5.3 | 214.3 ± 6.0 | 215.6 ± 6.6 | 227.3 ± 6.6* |

[a]Values represent mean body weight (gm) ± standard error. N = 5 animals.
[b]SPGLN designates soluble phosphorylated glucan.
*$p < 0.01$ lowing a single bolus injection. Control rabbits showed a mild decrease of 0.2° C. in body temperature. Rabbits treated with soluble phosphorylated glucan showed a mean increase of 0.44° C. Thus, there was a slight pyrogenicity seen in rabbits.

5.3.3. NON IMMUNOGENICITY

The interfacial ring test, designed to detect the presence of IgG antibodies, was used to evaluate the immunogenicity of soluble phosphorylated glucan when chronically administered to dogs for 120 days.

Serum samples were obtained from an adult female dog following 120 days chronic treatment with twice weekly intravenous injections of 5 mg/kg sterile, pyrogen-free soluble phosphorylated glucan. The interfacial ring precipitin test was performed as follows 0.1 ml of undiluted antisera was pipetted into test tubes. The antigen or phosphorylated soluble glucan at dilutions of 1:2, 1:4, 1:8,.1:16 and 1:32 was layered onto the anti-sera to form straight interface. Formation of a white precipitin ring at the interface indicates the presence of antibody specific for the glucan. No precipitin ring was detected at any antigen dilution.

5.4. USES OF SOLUBLE PHOSPHORYLATED GLUCAN

Because soluble phosphorylated glucan influences very fundamental host defense systems of the body regulating the number, functional activity and interaction of macrophages, T and B lymphocytes, leukocytes and natural killer cells as well as their humoral and secretory components, it possesses the potential for non-specifically modifying an extensive array of diseases including infectious and neoplastic diseases.

Soluble phosphorylated glucan demonstrates a number of characteristics which make it particularly advantageous for the prohpylactic and therapeutic treatment of neoplasms including, but not limited to the following advantages:

(1) Soluble phosphorylated glucan exerts direct inhibitory effects on the proliferation of tumor cells including, but not limited to lymphocytic leukemic cells, melanoma cells and reticulum cell sarcoma cells;

(2) Soluble phosphorylated glucan has very low toxicity;

(3) Soluble phosphorylated glucan prevents and corrects the development of leukopenia;

(4) Soluble phosphorylated glucan enhances a variety of diverse aspects of cellular and humoral immune responses of the host; and (5) Soluble phosphorylated glucan prevents or reverses the development of immunosuppression in the host.

Due to the stimulation of macrophage phagocytic and secretory activity and increased proliferation of macrophages caused by soluble phosphorylated glucan, this composition can advantageously be used either alone or in combination with other modalities such as surgery and chemotherapy, to treat malignant neoplastic diseases including, but not limited to adenocarcinoma, reticulum cell sarcoma, melanoma, lymphocytic leukemia, etc.

Soluble phosphorylated glucan has additive or synergistic effects when used in combination with a broad range of antitumor or anticancer agents. Additionally soluble phosphorylated glucan is effective in preventing and/or correcting the development of leukopenia which is often associated with the use of a variety of antitumor or anticancer agents. Table 5 illustrates some of the antitumor or anticancer agents that may be used in combination with soluble phosphorylated glucan. Table 5 is in no way intended to be an exhaustive list. Additionally, a combination of one or more antitumor or anticancer agents may be used together with soluble phosphorylated glucan.

TABLE 5
EXAMPLES OF ANTI-TUMOR AGENTS WHICH MAY BE COMBINED WITH SOLUBLE PHOSPHORYLATED GLUCAN FOR TREATMENT OF NEOPLASIAS

I. ALKYLATING AGENTS
  CLASSIC ALKYLATING AGENTS
    Bis (chloroethyl) amines
    Asaley
    Chlorambucil
    Cyclophosphamide (CTX)
    Ifosfamide
    Mechlorethamine (HN$_2$)
    Melphalan (1-PAM)
    Uracil mustard
    Ethyleneimines
    Triethylene thiophosphoramide (Thio-TEPA)
  CLASSIC ALKYLATING AGENTS
    Alkyl sulfonates
    Busulfan
    Yoshi 864
  NITROSOUREAS
    Carmustine (BCNU)
    Estramustine
    Lomustine (CCNU)
    Semustine (Me-CCNU)
    Streptozocin
    Chlorozotocin
  ANTITUMOR ANTIBIOTICS
    Anthracyclines
    Doxorubicin
    Daunorubicin (Adriamycin)
    Rubidazone
    Carminomycin
    Aclacinomycin
    Chromomycin A$_3$
    Dactinomycin
    Mithramycin
    Mitomycin C
    Piperazinedione
    Bleomycins
    4'-Epiadriamycin
    4'-Deoxyadriamycin
    Neocarzinostatin
    Bisantrene
    2'-Deoxycoformycin
    Actinomycin
    Mitoxantrone
  MISCELLANEOUS ALKYLATOR AGENTS
    Cisplatin
    Dacarbazine (DTIC)
    Galactitol
    Hexamethymelamine
    Pipobroman
II. ANTIMETABOLITIES
  FOLATE ANTAGONISTS
    Ethanesulfonic acid compound (Baker's antifol)
Methotrexate (MTX)
Dichloromethotrexate
Aminopterin
PURINE ANTAGNOSITS
Azathioprine
Mercaptopurine (6-MP)
Thioguanine (6-TG)
5-Azacytidine
Cyclocytidine
III. PLANT ALKALOIDS
Vinblastine
Vincristine
Vindesine
Etoposide (VP-16-213)
VM-26 (teniposide)
Maytansine
IV. MISCELLANEOUS AGENTS
Cytembena
Hydroxyurea
Razoxane
Asparaginase
Procarbazine
Cytarabine (ARA-C)
Fluorouracil (5-FU)
Floxuridine (FUDR)
Alpha-difluoromethylornithine
Azaribine Finally, soluble phosphorylated glucan is demonstrated (see Section 7) to stimulate the production and secretion of a soluble cytotoxic/cytostatic factor in macrophage cells (hereinafter, macrophage cytotoxic factor "MCF"). MCF is a soluble protein fraction of unknown structure isolated from the supernatant culture medium of macrophage cells that is toxic to cancerous cells including but not limited to adenocarcinoma, etc. Thus, the soluble phosphorylated glucan may be advantageously used to stimulate MCF production in vivo. Additionally, soluble phosphorylated glucan can be used to stimulate production of MCF by macrophage cells in vitro.

5.5. ROUTES AND METHODS OF ADMINISTRATION

The soluble phosphorylated glucans of the present invention can be administered for prophylactic and therapeutic applications by a number of routes, including but not limited to: orally, by injection including but not limited to intradermally, intraveneously, intraperitoneally, subcutaneously, intramuscularly, etc., topically as a dry powder or in a suitable physiologic carrier, by topical application to nasal and nasopharyngeal linings, and by inhalation via aerosolization and application to respiratory tract linings, etc.

When administered to an animal or a human, the soluble phosphorylated glucan may be combined with water, an aqueous solution or any physiologically acceptable pharmaceutical carrier or vehicle. Moreover as described above, the soluble phosphorylated glucan may be administered in combination with an antitumor or anticancer agent. When a combination of soluble phosphorylated glucan and an antitumor agent is desired, each agent may be simultaneously administered, or soluble phosphorylated glucan may be combined with one or more antitumor agents and administered as a single composition. The combination may be administered for prophylactic and therapeutic applications by a number of routes, including but not limited to: orally, by injection including but not limited to intraveneously, intraperitoneally, subcutaneously, intramuscularly, intradermally, etc., topically as a dry powder or in a suitable physiologic carrier, by topical application to nasal and nasopharyngeal linings, and by inhalation via aerosolization and application to respiratory tract linings, etc.

According to other embodiments of the present invention, the soluble phosphorylated glucan either alone or in combination with an antitumor agent may be administered by a number of delivery modalities including but not limited to the following: incorporated into liposome vesicles; in combination with an albumin complex to increase the intravascular half-life, in combination with a targeting agent such as a polyclonal or monoclonal antibody against an antigen associated with a specific neoplasia etc.; in combination with an anhydrous lipid base for topical or parental administration, etc. In addition, the soluble phosphorylated glucan, either alone or in combination with a known antitumor agent can be impregnated on bandages, sutures or dressings either as a dry powder or in a suitable physiologic carrier.

The following series of Examples are presented for purposes of illustration and not by way of limitation on the scope of the invention.

6. PREPARATION OF SOLUBLE PHOSPHORYLATED GLUCANS

6.1. PREPARATION FROM PARTICULATE GLUCAN OBTAINED FROM SACCHAROMYCES

Particulate glucan was prepared from *Saccharomyces cerevisiae* according to the method of Di Luzio et al. (1979, Int'l J. Cancer 24: 773-779). Briefly, using a 6 l flask, 540 gm of dry yeast (Universal Foods Corp., Milwaukee, Wis.) was suspended in 3 l of 3% aqueous sodium hydroxide solution. The suspension was placed in boiling water bath 4 hours, cooled overnight and the supernatant decanted. This procedure was repeated three times. The residue was then acidified with 800 ml of concentrated hydrochloric acid plus 2 l of 3% hydrochloric acid and placed in a boiling water bath for 4 hours. The suspension was allowed to stand overnight and the supernatant decanted. The residue was further digested with 3 l of 3% hydrochloric acid at 100° C. for 4 hours, cooled overnight and decanted. The 3% hydrochloric acid digestion was repeated twice. The residue was then washed three times with distilled water (20° C.) and twice with distilled water at 100° C. One l of ethyl alcohol was added to the residue, mixed thoroughly and allowed to stand a minimum of 24 hours for maximum extraction. The dark reddish-brown alcohol supernatant was aspirated from the residue and discarded. The alcohol extraction procedure was repeated until the alcohol supernatant was essentially colorless. The alcohol was removed by washing the residue four times with hot water; the particulate glucan preparation was then collected by centrifugation, frozen and lyophilized.

Soluble phosphorylated glucan was prepared according to the method described in Section 5 by solubilization and phosphorylation of the particulate glucan as follows:

18 gm of urea (6M) was dissolved in a flask containing 50 ml dimethylsulfoxide (DMSO) with constant stirring. One gm of particulate glucan was added to form a finely divided suspension. The flask was heated to 100° C. and 10 ml of phosphoric acid (85%) was added slowly dropwise. The mixture was maintained at 100° C. for 3-12 hours by immersion in a boiling water bath. It is preferred to allow the reaction to proceed for about 6 hours.

During the heating process, a precipitate was formed which became visible after about 1 hour and increased in amount thereafter. After about 6 hours, the mixture was cooled and diluted with 200 ml distilled water to resuspend the precipitate. The mixture was then filtered through coarse, medium and fine sintered funnels to remove the precipitate.

The resulting solution was then molecularly sieved in order to remove low molecular weight (MW) fractions including glucose, DMSO and urea.

In one series of experiments, molecular sieving was accomplished by dialysis for 5 days against running distilled water using Spectrapor membrane dialysis tubing (Fisher Scientific Co; Pittsburgh, Pa.). The MW size range of pores of this tubing is about 12,000 daltons. In another series of experiments, molecular sieving was accomplished using a Millipore dialyzer/concentrator (Millipore Corp., Bedford, Mass.) with a 10,000 MW membrane filter. About 70 l of dialyzing solution were used to remove low MW compounds. In either case, tests for the presence of glucose in the final preparation were negative. Moreover, using high performance gas-liquid chromatography, no DMSO was detectable in the final preparation.

Following molecular sieving, the solution containing the phosphorylated soluble glucan was concentrated and lyophilized. This phosphorylated glucan is stable in a lyophilized state for at least 2 years and at least for 15 months in solution maintained at −20° C.

6.2. PREPARATION FROM *CORIOLUS VERSICOLOR*

Soluble phosphorylated glucan was prepared from a basidiomycete *Coriolus versicolor* (Fr. Quel.) as follows:

A commercially available polysaccharide-protein preparation termed "Krestin" or "PSK" obtained from Sanyko Corporation, Tokyo, Japan, was used as the starting material for the preparation of soluble phosphorylated glucan from *C. versicolor*. This commercial preparation of a relatively crude preparation comprising a beta-1,4, beta-1,3, beta-1,6,-glucan-protein complex. The principal chemical structure of the polyglucose is a main chain of glucose units linked by 1-4 glucosidic bonds, having attached branch or side chains of glucose units linked by beta-1,3 and beta-1,6 glucosidic bonds. The protein content ranges from 15-38%. (Ehrke et al., 1983, Internat'l J. Immunopharm. 5: 34-42; Yamaura and Azuma, 1982, Adv. Immunopharm. 2: 501-507).

Because the commercially available PSK preparation is relatively crude preparation and has a relatively high protein content, intraveous administration of this material is not possible. It must be administered orally.

The PSK polysaccharide-protein complex from *C. versicolor* was prepared as a soluble phosphorylated glucan (hereinafter "soluble phosphorylated-PSK") as described in Section 5. The isolated soluble phosphorylated-PSK was lyophilized.

6.3. PREPARATION FROM SCLEROTIUM

Soluble phosphorylated glucan was prepared from *Sclerotium glucanium* as follows:

A commercially available sclero-glucan termed "Polytran R" obtained from Jetco Chemicals, Inc. (Corsicana, Tex.) was used as the starting material. This commercial preparation is a monionic polyglucose of greater than 500,000 daltons MW comprising a linear chain of glucose units linked by beta 1-3 glucosidic bonds in which about 30-35% of the linear chains have appended a single glucose unit linked via a beta 1-6 linkage. When mixed with water or an aqueous solution, Polytran R forms a colloidal suspension that becomes increasingly viscous over a 24 hour period. Because of the formation of such viscous gel, Polytran R is not useful for intravenous administration. A novel, rapid process was used to obtain a colloidal glucan from the sclero-glucan as follows:

One hundred forty grams Polytran R was added to 2.0 liters of 1M NaOH, pH about 14 with constant stirring on a hot plate. The mixture was maintained at room temperature for 4 days. Then the mixture was heated to about 85° C. for about 20 minutes, during which time a dark brown color developed in the mixture. After the mixture was cooled to room temperature, it was filtered through coarse and then medium sintered glass funnels. The filtrate was then passed serially through a series of Millipore filters: 3.0, 1.2, 0.8 and 0.65 microns. The resulting clear filtrate had a dark amber color. An aliquot (500 ml) was diluted to 6.0 liters in a dialyzing flask and dialyzed against 40 liters of ultra-pure water. The pH of the final concentrated mixture was about 6.7. The colloidal glucan isolated, a light brown spongy material, was lyophilized.

Soluble phosphorylated glucan was prepared from the colloidal glucan as described in Section 5.

In practice, 72 gm of urea (6M) was dissolved in a flask containing 200 m DMSO with constant stirring. Four gm of colloidal glucan was added to form a finely divided suspension. The flask was heated to 100° C. and 40 ml of phosphoric acid (85%) was added slowly drop wise. The mixture was maintained at 100° C. for 6.0 hours.

During the heating process, a precipitate was formed which became visible and quite noticeable after about 3 hours and increased in amount thereafter. After about 6 hours, the mixture was cooled, and diluted with 4 liters distilled water to resuspend the precipitate. The mixture was then filtered through a 3.0 micron filter.

The resulting solution was molecularly sieved in order to remove low molecular weight fractions. In one series of experiments molecular sieving was accomplished by dialysis (1 liter: 5 liters water).

Following molecular sieving, the solution containing the soluble phosphorylate glucan was concentrated and lyophilized to yield about 4 gms soluble phosphorylated glucan.

7. IMMUNOBIOLOGICAL PROPERTIES OF SOLUBLE PHOSPHORYLATED GLUCANS

In all experiments reported below, animals were maintained on Purina Laboratory Chow ad libitum in air-conditioned rooms maintained on 12 hour light/dark cycles.

7.1. MODIFICATION OF ENHANCED SUSCEPTIBILITY TO OPPORTUNISTIC INFECTIONS IN IMMUNOSUPPRESSED ANIMALS

Animals which are immunosuppressed either because of chemotherapy, congenital or acquired immunodeficiency (e.g., acquired immunodeficiency syndrome or AIDS) are susceptible to infection by a variety of opportunistic organisms. For exmmple, a major cause of death in patients suffering AIDS is pneumonia caused by *Penumocystis carinii* (see e.g., Jaffee et al., 1983, J. Infect. Dis. 148:339-345; Gottlieb et al., 1981, New Eng. J. Med. 305:1425-1431).

Previous studies by Walzer et al. (1983, J. Reticuloendothel. Soc. 33:1-9; 1979; Infec. Immunol. 24:939-947) have demonstrated that when immunosuppressed by chronic administration of a corticosteroid, the C3H/HeJ strain of mice is more susceptible to pneumonia induced by *P. carinii* than are other mouse strains. In these animals, like man, development of Pneumocystis pneumonia represents activation of latent infection due to the development of immunosuppression.

The following experiments demonstrate that administration of soluble phosphorylated glucan to chronically immunosuppressed C3H/HeJ mice significantly enhanced survival and reduced susceptibility of these animals to opportunistic infections.

7.1.1. ENHANCED SURVIVAL

In one series of experiments, 100 C3H/HeJ mice (Jackson Laboratories, Bar Harbor, Me.) were divided into 4 groups of 25 mice each. Group 1 received 0.5 ml of a 5% glucose solution intravenously; Group 2, 5 mg soluble phosphorylated glucan intravenously; Group 3, 1.5 mg cortisone acetate (Upjohn, Kalamazoo, Mich.) subcutaneously; and Group 4, both 5 mg soluble phosphorylated glucan intravenously and 1.5 mg cortisone acetate subcutaneously. All mice were treated twice weekly for 5 weeks, and survival was monitored for 60 days. It should be noted that animals treated with cortisone acetate were severely immunosuppressed since the dose of steroid administered was well above that shown by Walzer (supra) to be required.

Figure 3:
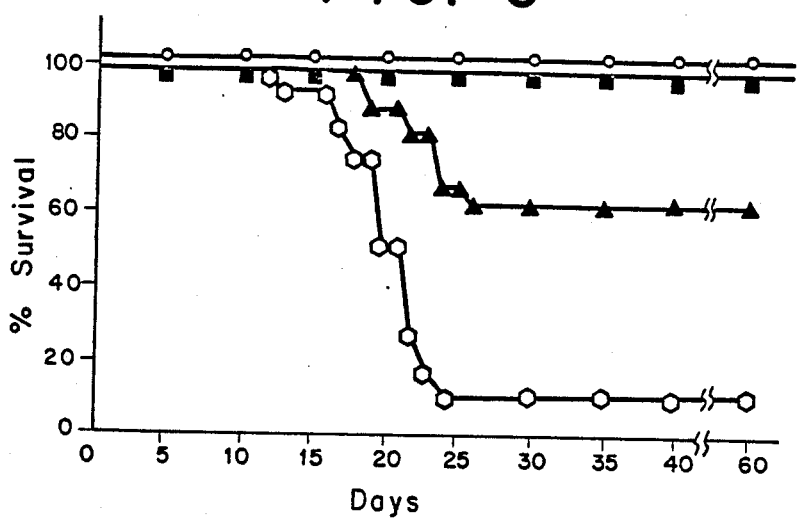
FIG. 3 is a graph illustrating the effect on survival of corticosteroid-immunosuppressed mice receiving twice weekly injections of soluble phosphorylated glucan.

Results are illustrated in FIG. 3. As demonstrated in FIG. 3, there was no mortality in mice treated either solely with glucose (Group 1) or soluble phosphorylated glucan (Group 2). By day 24, survival of mice treated with corticosteroid alone was 12% (Group 3). Histopathological studies indicated that contributing causes of death were bacterial and fungal infections, including those of the brain. In contrast, by day 24, survival in mice treated with corticosteroid and soluble phosphorylated glucan was about 68% (Group 4). Long term survival of such mice was 66%, highly statisically significant when compared to corticosteroid-treated mice (p 0.001).

7.1.2. ENHANCED RESISTANCE OF IMMUNOSUPPRESSED MICE TO ESCHERICHIA COLI INFECTION

The following experiment demonstrates that administration of soluble phosphorylated glucan enhanced resistance of both normal and chronically immunosuppressed mice to infection by *E. coli*.

Sixty C3H/HeJ mice were divided into 4 groups of 15 mice each. Group 1 received three injections of 5% glucose (0.5 ml) intravenously; Group 2, three injections of 4 mg/animal soluble phosphorylated glucan intravenously; Group 3, three injections of 1.5 mg/animal cortisone acetate subcutaneously; and Group 4, three injections of a combined 4 mg/animal soluble phosphorylated glucan intravenously and 1.5 mg/animal cortisone acetate subcutaneously at three day intervals. Three days following the last injection, the mice received $2.5 \times 10^7$ *E. coli* bacteria intraperitoneally. Survival was monitored for 15 days post-infection with *E. coli*.

Figure 4:
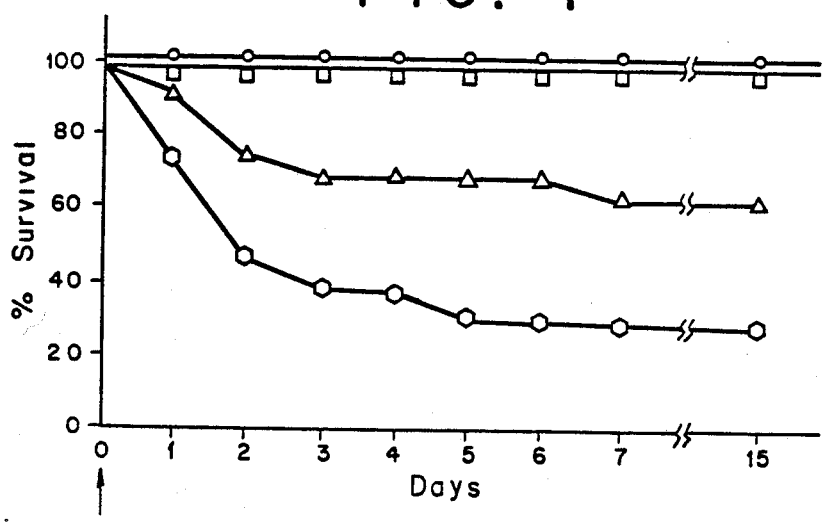
FIG. 4 is a graph illustrating the effect of prior in vivo administration of soluble phosphorylated glucan on resistance of both normal and corticosteroid-immunosuppressed mice to *Escherichia coli* infection.

Results illustrated in FIG. 4 demonstrate 65% survival in normal glucose-treated mice infected with *E. coli* (Group 1). No deaths occurred in this group after 7 days post-infection with *E. coli*. In contrast, 0% mortality was observed in normal mice treated with soluble phosphorylated glucan (Group 2). Thus, pretreatment with soluble phosphorlylated glucan significantly enhanced resistance to *E. coli* infection in normal animals.

Results presented in FIG. 4 also demonstrate marked mortality of mice chronically immunosuppressed by administration of corticosteroid. In immunosuppressed mice treated with glucose (Group 3), 50% mortality was noted at 40 hours and 75% mortality, at 5 days. In marked contrast, in immunosuppressed mice treated with soluble phosphorylated glucan (Group 4) 0% mortality was observed. Thus in both control and cortisone-treated mice, soluble glucan was able to enhance host resistance resulting in complete protection to a gram-negative infection both in normal and cortisone-immunosuppressed mice.

These studies demonstrate that the administration of soluble glucan to mice receiving immunosuppressive doses of cortisone results in modification of the cortisone-induced susceptibility to infection. Therefore, soluble phosphorylated glucan is capable of modifying not only the immunosuppressive effects of chronic administration of cortisone leading to decreased mortality from spontaneous infections, but also the relatively acute immunosuppressive effects of cortisone.

7.2. ENHANCEMENT OF MACROPHAGE PHAGOCYTIC ACTIVITY

The following experiment demonstrates that administration of soluble phosphorylated glucan significantly enhanced phagocytic function of macrophages.

Twenty male ICR mice were divide into two groups of 10 each. At 3, 2 and 1 day prior to determiniation of phagocytic activity, Group 1, designated control received injections of isovolumetric saline; Group 2, soluble phosphorylated glucan (200 mg/kg). All injections were administered intravenously.

Phagocytic function was evaluated by measuring the rate of intravascular clearance of colloidal carbon (C11/143 (a), Gunther Wagner, Hanover, Germany) according to the method of Wooles et al. (1962, Rad. Res. 16: 546-554). Colloidal carbon was administered (640 mg/kg) intravenously and serial blood samples were obtained from tail veins. Aliquots were hemolyzed in 4.0 ml of 0.5% sodium carbonate and the concentration of colloidal carbon was determined spectrophotometrically. The half-time (t/2) was taken as the time at which the optical density or concentration was one-half the zero time value as determined by extrapolation of the clearance curves to zero time. Results are presented in Table 6.

TABLE 6

| EFFECT OF SOLUBLE PHOSPHORYLATED GLUCAN ON MACROPHAGE PHAGOCYTIC FUNCTION | | | |
|---|---|---|---|
| Treatment[a] | Body Weight (gm) | Liver Weight (gm) | Intravascular Clearance t/2 (minutes) |
| Saline | 24.8 ± 0.82 | 1.94 ± 0.05 | 7.6 ± 0.73 |
| Soluble Phosphorylated | 25.2 ± 1.03 | 1.82 ± 1.03 | 3.5 ± 0.58* |

TABLE 6-continued

EFFECT OF SOLUBLE PHOSPHORYLATED GLUCAN ON MACROPHAGE PHAGOCYTIC FUNCTION

| Treatment[a] | Body Weight (gm) | Liver Weight (gm) | Intravascular Clearance t/2 (minutes) |
|---|---|---|---|
| Glucan | | | |

[a]N = 10 per group.
*p < 0.001

As demonstrated in Table 6, administration of soluble phosphorylated glucan significantly enhanced phagocytic function as reflected by a 55% increase in clearance (Table 6). As previously observed, no increase in liver weight occurred (Table 6).

7.3. ENHANCEMENT OF MACROPHAGE SECRETORY ACTIVITY

A major secretory product of macrophages, particularly in an activated state, is a mediator molecule called Interleukin I. Interleukin I is a polypeptide which induces, both in experimental animals and man, an acute phase protein response. This response includes increased erythrocyte sedimentation rates, leukocytosis, elevated acute phase proteins, and development of fever due to endogenous pyrogen. Additionally, Interleukin I has the ability to profoundly stimulate T-cell activation and proliferation. Thus, Interleukin I is a lymphocyte activating factor capable of cellular recruitment and, hence, enhances host defense activity.

The following experiment demonstrates that administration of soluble phosphorylated glucan stimulates macrophage secretory activity as assayed by the secretion of Interleukin I.

A number of rats (16) were injected intravenously with soluble phosphorylated glucan (200 mg/kg). Eight control animals received isovolumetric glucose. Plasma samples were obtained at 1, 3, 5, 8, 24, 48, 72 and 168 hours post-injection.

Production of Interleukin I was evaluated employing C-57BL/6J thymocytes. Cultures of thymocytes ($1 \times 10^6$ cells) were incubated with media alone, or with 0.1 ml plasma from control or soluble phosphorylated glucan-treated rats. The cell cultures were maintained for 24 hours, at which time 1 uCi of $^3$H-thymidine was added, and incubation was carried out for another 24 hour period. At that time, thymidine uptake was measured. Results are presented in FIG. 5.

Figure 5:
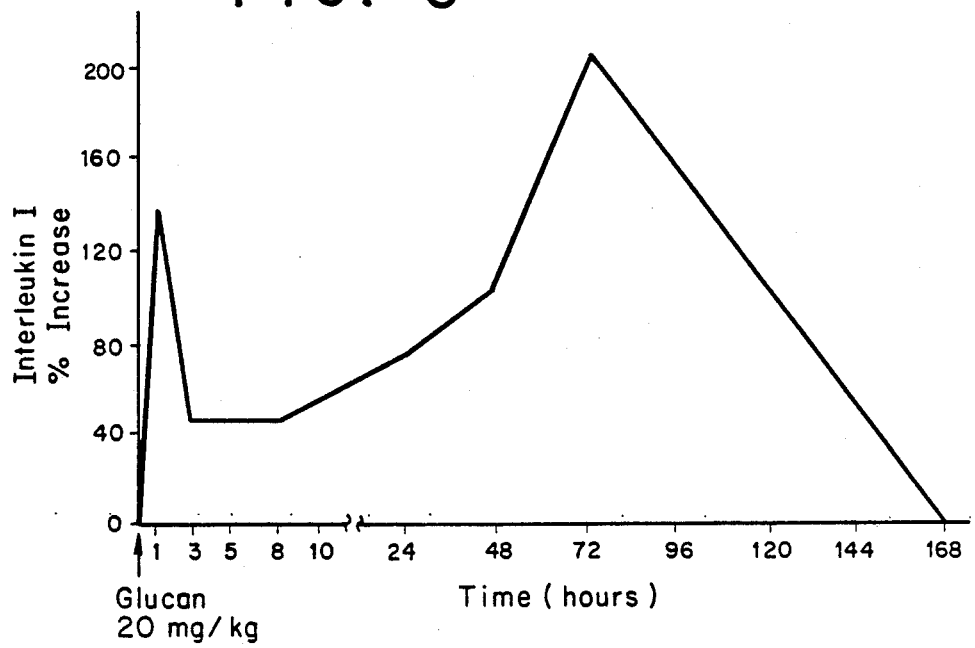
FIG. 5 is a graph showing the effect of soluble phosphorylated glucan on Interleukin I production.
Figure 6:
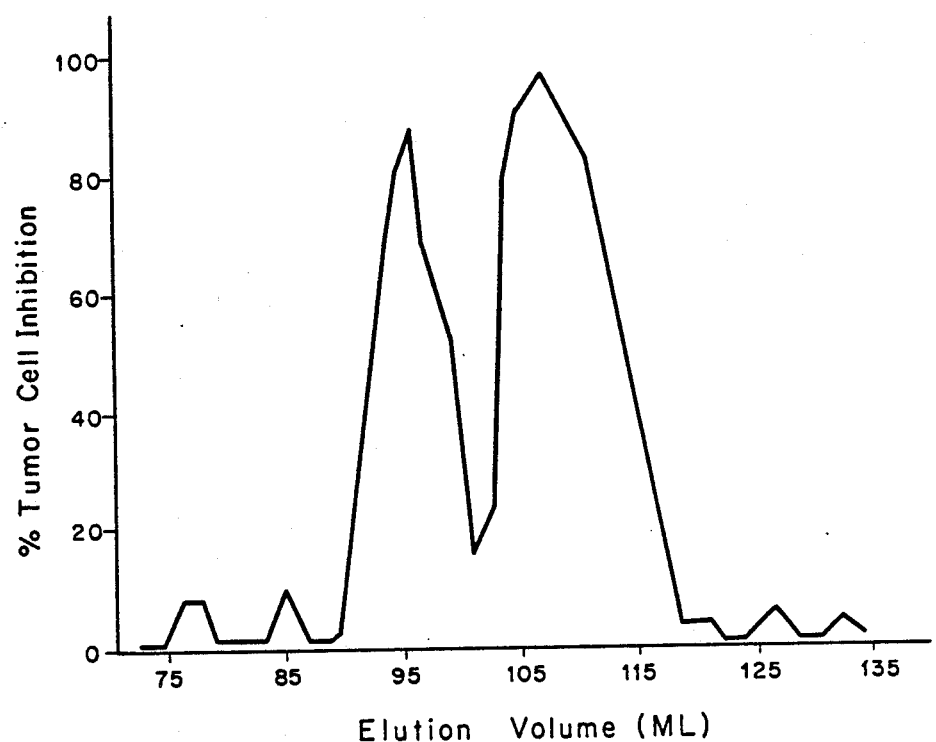
FIG. 6 is a chart showing that the tumor cell cytotoxic/cytostatic factor obtained from soluble phosphorylated glucan-activiated macrophage cultures consists of two major fractions with molecular weights of 38,500 and 84,000 daltons.

As illustrated in FIG. 5, serum obtained from soluble phosphorylated glucan-treated rats showed increased Interleukin I activity as reflected by the elevation in thymidine uptake by thymocytes at 1, 24, 48 and 72 hours compared to serum obtained from rats treated with glucose. Thus, soluble phosphorylated glucan rapidly activates macrophages and increases secretory activity, as reflected by elevated plasma interleukin levels. The nature of the 24-72 hour peak remains to be established.

7.4. ENHANCEMENT OF ANTI-TUMOR CYTOTOXIN PRODUCTION BY MACROPHAGES IN VITRO

The following experiments were conducted to evaluate the production of macrophage cytotoxic/cytostatic factors (MCF) by macrophages under the stimulation of soluble phosphorylated glucan.

Splenic macrophages, obtained from C57BL/6J mice, ($5 \times 10^6$ cells) were incubated with RPMI 1640 media with 7.5% Fetal Calf Serum, 50 IU/ml penicillin G, 50 ug/ml streptomycin, 50 ug/ml gentamycin sulfate, 10 ug/ml Amphotericin B, and 2 mg/ml NaHCO$_3$. Control cells were incubated with media alone. Experimental cells were incubated in media containing soluble phosphorylated glucan (5 mg/ml). All cell cultures were maintained for 20 hours at 37° C., under 5% CO$_2$, 95% air in Falcon 2013 culture flasks. After incubation, the culture supernatant was collected by centrifugation and all cells removed by passage through a 0.22 u filter.

In the assay for the presence of MCF, adenocarcinoma cells (BW10232) were labeled with $^3$H-thymidine and washed three times to remove any unincorporated radioactivity. The labeled tumor cells ($2 \times$ cells $10^4$ in 0.1 ml) were then added to microtiter wells, the supernatants to be tested for MCF were added in 0.1 ml volmmes, and the cells were incubated for 24 hours. After incubation the microtiter plates were centrifuged and 0.1 ml aliquots assayed for radioactivity. The released radioactivity, representing an index of tumor cells lysis, varies directly with the amount of MCF present. Additonally, qualitative evaluation of the degree of cytolysis and cytostasis was obtained by fixing tumor cells with ethanol and staining with giemsa. Results are presented in Table 7.

Supernatant from control or resting macrophages, i.e., non-soluble phosphorylated glucan-treated, contains a cytotoxic factor (MCF) which enhances the release of $^3$H-thymidine from adenocarcinoma cells when compared with media alone (Table 7). Supernatant from glucan-stimulated macrophages, however, produces substantially more MCF. A significant enhancement in cytotoxicity is manifested. (Table 7).

TABLE 7

ENHANCED CYTOTOXICITY OF SOLUBLE PHOSPHORYLATED GLUCAN(SPGLN)-ACTIVATED MACROPHAGE SUPERNATANT AGAINST ADENOCARCINOMA BW10232

| % $^3$H—Thymidine Release[a] | | |
|---|---|---|
| Media Control | Supernatant Resting Macrophages | Supernatant SPGLN-Activated Macrophages |
| 27.2 ± 2.8 | 53.4 ± 6.6* | 88.9 ± 3.7** |

[a]Values represent mean ± S.E. for 6 replicates per group.
*p < 0.01
**p < 0.001

In an effort to demonstrate that the enhanced cytolytic effect of the supernatant fraction was not due to a direct effect of glucan, $^3$H-thymidine labeled tumor cells were incubated in the presence of 0.5 mg of soluble phosphorylated glucan for 24 hours. Results are presented in Table 8.

TABLE 8

ABSENCE OF DIRECT CYTOTOXIC EFFECT OF SOLUBLE PHOSPHORYLATED GLUCAN ON ADENOCARCINOMA BW10232 IN VITRO

| % $^3$H—Thymidine Release[a] | |
|---|---|
| Media Control | Soluble Phosphorylated Glucan |
| 27.2 ± 2.8 | 22.4 ± 1.8 |

[a]Values represent means ± S.E. for 6 replicates per groups.

As can be observed in Table 8, soluble phosphorylated glucan had no significant effect on the release of thymidine from pre-labeled tumor cells. It can, therefore, be concluded that the enhanced release of thymidine by tumor cells was due to a macrophage produced product in the supernatant from cells cultured with soluble phosphorylated glucan.

Confirmation of the cytotoxic/cytostatic effects of the supernatant fraction was obtained by histological evaluation of the cultures. Excellent growth was apparent in adenocarcinoma cells (BW 10232) cultured in media alone. In accord with the previously described data relating to $^3$H-thymidine release, normal growth was also apparent in tumor cells cultured for 24 hours with media containing soluble phosphorylated glucan. This confirms the absence of a direct cytotoxic effect of souble phosphorylated glucan on the tumor cell line. In markdd contrast, significant cell injury and lysis was apparent in tumor cells incubated with the supernatant from macrophage cultures treated with soluble phosphorylated glucan. The degree of cell injury and lysis observed in such tumor cell cultures was considerably greater than that observed when supernatant from normal or control macrophages was added to the culture medium. Thus, soluble phosphorylated glucan induced resting macrophages to increase their production of a tumor cytolytic factor.

Since the cytotoxic/cytostatic factor MCF was found to be a protein, studies were undertaken to define its properties, such as molecular weight(s). Fifty mg of the dried supernatant from macrophage cell cultures was dissolved in 1 ml of sterile water and added to a 1.5 cm$\times$90 cm glass column (LKB Instruments) packed with Sephacryl S-300 superfine matrix (Pharmacia Fine Chemicals, Piscataway, N.J.). The column was operated at a flow rate of 0.2 ml/min using phosphate buffered saline as the eluent. Fractions were collected at 1 ml intervals and tested for cytostatic activity. Results are graphically illustrated in FIG. 9.

As shown in FIG. 9, the column chromatography of soluble phosphorylated glucan-activated macrophage culture supernatant yielded 2 peaks with cytotoxic activity against adenocarcinoma cells. The peaks elute at volumes indicative of molecular weights of 38,500 and 84,000 daltons.

7.5. ENHANCEMENT OF KUPFFER CELL TUMORICIDAL ACTIVITY

The following experiment demonstrates that administration of soluble phosphorylated glucan in combination with an anti-cancer agent such as cyclophosphamide significantly enhanced Kupffer cell tumoricidal actiiity when determined in an in vitro assay.

Thirty two male C57BL/6J mice were divided into four groups of eight each. Group 1, designated control, received dextrose (5% w/v); Group 2, soluble phosphorylated glucan (200 mg/kg) in dextrose; Group 3, cyclophosphamide (45 mg/kg; Mead-Johnson, Evansville, Ind.) in dextrose; and Group 4, soluble phosphorylated glucan (200 mg/kg) plus cyclophosphamide (45 mg/kg) in dextrose on days 0, 3, 6 and 9. Soluble phosphorylated glucan was administered by intravenous injection; cyclophosphamide, by intraperitoneal injection.

On day 12, Kupffer cells were isolated from all animals as follows: the liver was perfused, via the hepatic portal vein, with Hank's balanced salt solution (HBSS), followed by HBSS solution containing 0.125% ((w/v) collagenase Type IV (Sigma Chemical Co., St. Louis, Mo.). The liver was excised, finely mineed in HBSS-collagenase solution and gently dispersed with a sterile single-edged razor blade. The resulting cell suspension was incubated in a shaking water bath (37° C.) for 40 minutes. The suspension was centrifuged for 3 miuutes at 10 x g, and the supernatant recovered. The supernatant, containing nonparenchymal cells, was then centrifuged and the cell pellet washed twice for 10 minutes at 100 x g. The cell pellet was suspended in 17.5% (w/v) metrizamide (Accurate Chemical and Scientific Corp., Westbury, N.Y.) in HBSS. The metrizamide gradient was overlaid with 0.5 ml of HBSS and centrifuged at 500 x g for 20 minutes at room temperature. Kupffer cells form a band at the interface of the metrizamide-HBSS. The cells were aspirated and the cell pellet was washed three times with RPMI 1640. The cell suspension was incubated in a Falcon plastic petri dish for 1 hour at 37° C. under 5% $CO_2$. The plate was then gently washed with RMPI 1640 medium twice to remove non-adherent cells. The adherent Kupffer cells thus obtained were diluted to a concentration of $1\times10^7$/ml.

An in vitro assay of the tumoricidal activity of the Kupffer cells from the treated animals was performed as follows: Sarcoma M5076 cells, cultured in vitro for several days were labeled by incubation with $^3$H-thymidine (6.1 Ci/mmole, New England Nuclear, Boston, Mass.) in RPMI 1640 for 72 hours. The $^3$H-thymidine-labeled sarcoma cells were recovered by centrifugation, washed and resuspended in RPMI 1640.

$^3$H-thymidine-labeled sarcoma cells M5076 ($2\times10^4$/well) and Kupffer cells ($1\times10^6$/well) were added to microtiter wells. The wells were incubated for 72 hours at 37° C. under 5% $CO_2$. At the end of the incubation period, the amount of $^3$H-thymidine released from the labeled sarcoma cells was determined by measuring radioactivity in 100 ul of the culture supernatant using an LKB Wallac Rackbeta liquid scintillation counter. Results are presented in Table 9.

TABLE 9

ENHANCEMENT OF KUPFFER CELL IN VITRO TUMORCIDAL ACTIVITY FOLLOWING GLUCAN CYCLOPHOSPHAMIDE ADMINISTRATION[a]

| Group | % $^3$H—Thymidine Release |
| --- | --- |
| Control | 27 ± 1 |
| Soluble Phosphorylated Glucan | 22 ± 4 |
| Cyclophosphamide | 28 ± 3 |
| Soluble Phosphorylated Glucan + Cyclophosphamide | 33 ± 3* |

[a]C57BL/6J mice were injected with soluble phosphorylated glucan (200 mg/kg), cyclophosphamide (45 mg/kg) or soluble phosphorylated glucan and cyclophosphamide on days 0, 3, 6 and 9. Kupffer cells were isolated and assayed for tumor cytotoxicity on day 12. Dextrose served as the control. Values represent the mean ± standard error. N = 8/group.
*p < 0.05.

As demonstrated in Table 9, Kupffer cells obtained from mice treated with soluble phosphorylated glucan in combination with cyclophosphamide showed an enhanced cytotoxicity (p<0.05) against sarcoma M5076 cells (33% release $^3$H-thymidine) compared to cells obtained from control animals (27% release $^3$H-thymidine). In contrast, Kupffer cells obtained from mice treated with either soluble phosphorylated glucan alone or with cyclophosphamide alone showed no significant difference in cell cytotoxicity against the sarcoma cells from cells obtained from control animals.

The majority of macrophage elements of the reticuloendothelial system exist as Kupffer cells in the liver sinusoids. Thus these results which demonstrate that soluble phosphorylated glucan and cycolphosphamide in combination activate Kupffer cell tumoricidal activity clearly indicate that such combination therapy may be important in prevention and defense against metastases of primary tumors to the liver.

7.6. ENHANCED PROLIFERATION OF BONE MARROW CELLS IN VITRO

This experiment demonstrates that administration of soluble phosphorylated glucan greatly enhanced proliferation of bone marrow cells when assayed in vitro. In addition, administration of soluble phosphorylated glucan in combination with cyclophosphamide enhanced in vitro proliferation of bone marrow cells in a synergistic fashion when compared to effects observed following administration of either agent alone.

Bone marrow cells were obtained from the four groups of male C5BL/6J mice described in Section 7.5, supra. Group 1, designated oontrol received dextrose (5% w/v): Group 2, 200 mg/kg soluble phosphorylated glucan; Group 3, 45 mg/kg cyclophosphamide (Mead-Johnson, Evansville, Ind.); and Group 4, 200 mg/kg soluble phosphorylated glucan and 45 mg/kg cyclophosphamide on days 0, 3, 6 and 9. Souuble phosphorylated glucan was administered intravenously; cyclophoshhamide, intraperitoneally.

Bone marrow cells were obtained from treated animals on day 12 by excising femurs and flushing the marrow cavity with 6 ml of RPMI 1640 culture medium. The bone marrow cells were centrifuged, washed twice and resuspended at a concentration of $1 \times 10^7$ cells/ml.

In vitro proliferation of bone marrow cells from the treated animals was assayed as follows: bone marrow cells were incubated in Corning 96 well microtiter plates ($1 \times 10^6$ cells/well for 40 hours at 37° C. under 5% $CO_2$. One uCi of $^3$H-thymidine was added for the final 8 hours of the incubation period. Following incubatoon, the plates were centrifuged and washed twice with RPMI 1640. Distilled water (200 ul) was added to each well and the plates were freeze-thawed three times. One hundred ul of the resulting supernatant was collected and radioactivity was determined using an LKB Wallac Rackbeta liquid scintillation counter. Results are illustrated in Table 10.

TABLE 10

ENHANCED BONE MARROW PROLIFERATION FOLLOWING GLUCAN CYCLOPHOSPHAMIDE ADMINISTRATION[a]

| Group | $^3$H—Thymidine Uptake (CPM) |
|---|---|
| Control | 451 ± 45 |
| Soluble Phosphorylated Glucan | 1631 ± 177* |
| Cyclophosphamide | 818 ± 104** |
| Soluble Phosphorylated Glucan + Cyclophosphamide | 2332 ± 371* |

[a]C57BL/6J mice were injected with soluble phosphorylated glucan (200 mg/kg), cyclophosphamide (45 mg/kg) or soluble phosphorylated glucan and cyclophosphamide on days 0, 3, 6 and 9. Bone marrow cells were harvested on day 12 and assayed for proliferation. Values represent the mean ± standard error. Dextrose served as the control. N = 28–32/group.
*p < 0.001
**p < 0.01

As demonstrated in Table 10, administration of soluble phosphorylated glucan alone resulted in a highly significant increase of bone marrow cell proliferation (261%; p<0.001) when compared to the control group. Administration of cyclophosphamide alone less markedly increased bone marrow cell proliferation (81%; p<0.01) when compared to the control group.

In addition, results illustrated in Table 10 clearly demonstrate that administration of soluble phosphorylated glucan and cyclophosphamide exerted a synergistic effect on bone marrow cell proliferation (417%; p<0.001) when compared to the control group. The enhanced bone marrow proliferation observed following administration of soluble phosphorylated glucan and cyclophosphamide in combination was significantly greater than either soluble phosphorylated glucan alone (43%; p 0.05) or cyclophosphamide alone (185%; p 0.01).

7.7. ENHANCEMENT OF SPLENOCYTE RESPONSE TO MITOGENS

This experiment demonstrates that administration of soluble phosphorylated glucan either alone or in combination with cyclophosphamide significantly enhanced splenocyte proliferation as well as the response of splenocytes to mitogens.

Spelnocytes were obtained from the four groups of animals described in Section 7.5, supra.

On day 12, spleens were excised aseptically, splenocytes were harvested by dispersing the spleens by gentle teasing and the cells suspended in RPMI 1640. Erythrocytes were removed by hypotonic lysis. Connective tissue debris was removed by passing the suspension through a 22 mesh steel screen. The cells were washed twice, centrifuged and diluted to $1 \times 10^7$ cells/ml. Splenocytes were incubated in Corning 96 well microtiter plates ($1 \times 10^6$ cells/well) in the presence of phytohemagglutinin (1 ug/well), pokeweed mitogen (1 ug/well) or concanavalin A (1 ug/well) for 64 hours at 37° C. and 5% $CO_2$ RMPI 1640 medium alone served as the control. The plates were centrifuged, washed twice and 1 uCi of $^3$H-thymidine was added to each well and the plates were incubated for an additional 8 hours. Following incubation, the plates were centrifuged and washed twice with RPMI 1640. Two hundred u of distilled water was added to each well and the plates were freeze-thawed three times. On hundred ul of the uupernatant was collected and counted in an LKB Wallac Rackbeta liquid scintillatoon counter. Results are illustrated in FIG. 7.

Administration of soluble phosphorylated glucan and cyclophosphamide on days 0, 3, 6 and 9 significantly enhanced in vitro splenocyte proliferation and splenocyte response to mitogens on day 12 (FIG. 7). Additionally, the combination of soluble phosphorylated glucan and cyclophosphamide exhibited significantly greater in vitro splenocyte proliferation and response to mitogens, than did either treatment alone. Splenocytes isolated on day 12 from C57BL/6J mice treated with soluble phosphorylated glucan-cyclophosphamide and incubated in the absence of mitogen showed a 174% (p<0.001) increase in $^3$H-thymidine uptake, when compared to controls (FIG. 7). Additionally, the combination of glucan-cyclophosphamide significantly enhanced splenocyte proliferation when compared to either glucan (107%) or cyclophosphamide (61%) as a single regimen (FIG. 7). Soluble phosphorylated glucan or cyclophosphamide as a single regimen showed significant 32% (p<.0.01) and 70% (p<0.001) increases in splenocyte uptake of $^3$H-thymidine, respectively.

Soluble phosphorylated glucan-cyclophosphamide also significantly (p<0.001) enhanced splenocyte response to the mitogens concanavalin A (ConA), phytohemagglutinin (PHA) and pokeweed mitogen by 224%, 331% and 184%, when compared to control splenocytes (FIG. 7). Furthermore, the combination of soluble phosphorylated glucan-cyclophosphamide significantly enhanced splenocyte proliferative response to mitogens, when compared to either glucan or cyclophosphamide as a single treatment regimen. Soluble phosphorylated glucan as a single regimen enhanced splenocyte response to PHA and pokeweed mitogen (PWM). Cyclophosphamide as a single regimen significantly ($p<0.001$) enhanced splnnocyte response to all mitogens tested.

7.8. MODIFICATION OF METASTATIC LIVER DISEASE

The following series of experiments demonstate that administration of soluble phosphorylated glucan either alone or in conjunction with an anti-cancer agent, e.g., cyclophosphamide, reduces growth of primary tumor and metastasis of reticulum cell sarcoma in mice.

One hundred twenty C57BL/6J mice (Jackson Laboratories, Bar Harbor, Me.) were divided into 4 groups of 30 each. All mice received subcutaneous injection of $1.0 \times 10^4$ reticulum cell sarcoma cells M5076. Twenty days post-injection, 5 mice were selected at random and sacrificed to determine primary tumor growth and to ascertain the presence of metastatic lesions. The average primary tumor weight was 1.86 gm or 6.4% of body weight, and all animals examined had organ specific liver micrometasases. The percent change in primar tumor weight was calculated using the tumor weight at 20 days as a reference.

At twenty days post-tumor transplantation and every 3 days until 50 days thereafter, Group 1, designated controls received glucos (0.5 ml) intraveneously; Group 2 received soluble phosphorylated glucan (200 mg/kg body weight) intravenously; Group 3 received cyclophosphamide (Cytoxan, Mead-Johnson, Evanvville, Ind.) (45 mg/kg body weight); and Group 4 received a combination of soluble phosphorylated glucan (200 mg/kg body weight) intraveneously and cyclophosphamide (45 mg/kg body weight) intraperitoneally.

Effects of various treatments on the growth of primary tumor are presented in Table 11. Effects on survival are presented in Table 12.

TABLE 11
SOLUBLE PHOSPHORYLATED GLUCAN-CYCLOPHOSPHAMIDE CHEMO-IMMUNOTHERAPY: SYNERGISTIC EFFECT ON PRIMARY TUMOR

| Treatment Group Number[a] | Tumor Weight (% of Body Weight) | |
|---|---|---|
| | Day 30 | Day 36 |
| 1 | 12.6 | 15.5 |
| 2 | 8.3 | 11.8 |
| 3 | 8.5 | 8.7 |
| 4 | 4.4 | 2.3 |

[a]All groups of C57BL/6J mice were subcutaneously injected with $1.0 \times 10^4$ reticulum sarcoma at day 0. At day 20, the mean weight of the primary tumor was 1.86 g or 6.4% body weight. At day 20 and every 3 days thereafter mice received the appropriate drug treatment. See text for details.

As demonstrated in Table 11, 30 days post-injection of reticulum sarcoma cells, soluble phosphorylated glucan and cyclophosphamide had about equivalent effect on reducing primary tumor growth, i.e., 8.3% and 8.5% as compared to 12.6% body weight in control mice (Group 1). In mice treated with a combination of soluble phosphorylated glucan and cyclophosphamide (Group 4), there was an even greater reduction in size of the primary tumor, i.e., 4.4% as compared to 12.6% in control (Group 1).

Results were even more remarkable at day 36 11). While mean tumor weight increased 142% in the sixteen days (day 20-36) in the control group (Group 1), the tumor weight in the group treated with soluble phosphorylated glucan group (Group 2) increased only 84%, and only 36% in the cyclophosphamide (Group 3). For the first time in our studies, actual regression of the primary tumor was manifested under the influence of combined chemotherapy and soluble phosphoyylated glucan immunotherapy. With combined therapy, $-64\%$ growth was observed, denoting primary tumor regression.

TABLE 12
SOLUBLE PHOSPHORYLATED GLUCAN-CYCLOPHOSPHAMIDE CHEMO-IMMUNOTHERAPY: EFFECT ON SURVIVAL OF MICE WITH ESTABLISHED RETICULUM CELL SARCOMA M5076

| Treatment Group Number[a] | Initial Mortality[b] | Median Survival Time (Days) | Time (Days) 100% Mortality |
|---|---|---|---|
| 1 | 27 | 34 | 52 |
| 2 | 32 | 41* | 67 |
| 3 | 43 | 51* | 65 |
| 4 | 52 | 64** | 102 |

[a]Procedures were identical to those used to obtain data presented in Table 11. All treatments were terminated at day 50.
[b]Mortality in soluble phosphorylated glucan and cyclophosphamide group was presumed due to residual splenic tumor cells which subsequently disseminated when therapy was terminated.
*$p < 0.01$
**$p < 0.001$ As demonstrated in Table 12, significantly enhanced survival ($p<0.01$) was observed in mice treated with either soluble phosphorylated glucan (Group 2) or cyclophosphamide alone (Group 3) compared to controls (Group 1). Further, a highly statistically significant ($p<0.001$) enhanced survival time was observed in those animals treated with a combination of soluble phosphorylated glucan and cyclophosphamide (Group 4).

These studies clearly indicate the effectiveness of combined chemo-and soluble phosphorylated glucan-immuno-therapy. Not only did regression of primary tumor growth occur, but also a reduction of metastatic disease as reflected by histopathological observations was noted. Hepatic mttastases, which were pronounced in the control group, were essentially absent in the soluble phosphorylated glucan-cyclophosphamide treated group. Additionally, a significant enhancement in survival (Table 12) was also observed as well as enhancement of the interval before the initial death occurred in the treated group.

7.9. ABILITY OF SOLUBLE PHOSPHORYLATED GLUCAN TO PREVENT CYCLOPHOSPHAMIDE-INDUCED LEUKOPENIA

Among the deleterious effects associated with the administration of almost all antitumor or antineoplastic agents are the induction of myelosuppression, leukopenia, and the increased susceptibility to infectious disease (see generally, Klastersky, ed., in Infection in Cancer Patients, Raven Press, N.Y., 1982, pp. 1-12).

As detailed in Section 7.8., it is possible to induce a syngergistic effect on primary tumors when soluble phosphorylated glucan is combined with cyclophosphamide treatment. One of the disadvantages associated with the use of cyclophosphamide in cancer patients is the development of leukopenia. In view of the demonstrated ability of diverse particulate and soluble polyglycans to enhance hemopoietic recovery in mice when administered either an hour before or one hour after 650 rads of Cobalt radiation (see Patchen, 1983, Surv. Immunol. Res. 2: 237–242; Patchen et al., 1984, J. Biol. Response Modifiers, 3: 627–733) studies were undertaken to determine whether soluble phosphorylated glucan would possess the ability to maintain the peripheral leukocyte level in animals receiving therapeutic and immunosuppressive doses of cyclophosphamide.

Forty mice were subdivided into four gooups. Group 1, control mice, received intravenous isotonic glucose. Group 2 received soluble phosphorylated glucan (5 mg per mouse); Group 3, cyclophosphamide (Cytoxan) intraperitoneally (0.6 mg per mouse); and Group 4, combined therapy of cyclophosphamide plus soluble phosphorylated glucan. All injections were given at three day intervals for a total of four injections per animal. Total leukocyte counts of peripheral blood were made on day 14. The results of this study are presented in Table 13.

TABLE 13
PREVENTION OF CYCLOPHOSPHAMIDE-INDUCED LEUKOPENIA BY SOLUBLE PHOSPHORYLATED GLUCAN[a]

| Treatment | Total Leukocytes (in thousand per cu. mm of blood) |
|---|---|
| Control | 13.8 ± 1.6 |
| Soluble phosphorylaged Glucan | 10.0 ± 1.8 |
| Cyclophosphamide | 6.0 ± 0.8* |
| Soluble Phosphorylated Glucan + Cyclophosphamide | 12.2 ± 1.6** |

[a]Soluble phosphorylaged glucan (5 mg/mouse) was administered intravenously every third day. Cyclophosphamide (0.6 mg/mouse) was administered intraperitoneally every third day. Total leukocytes count were made on day 14 of the experiment.
*$P < 0.01$ - control compared with cyclophosphamide treatment.
**$P < 0.01$ - Soluble Phosphorylated Glucan + cyclophosphamide compared with cyclophosphamide alone.

As demonstrated, administration of cyclophosphamide produced a characteristic 47% decrease in total number of peripheral leukocytes ($P<0.01$). The administration of soluble phosphorylated glucan together with cyclophosphamide resulted in a 103% increase in total number of leukocytes compared with the cyclophosphamide-treated group ($P<0.01$).

This study clearly indicates that the simultaneous administration of soluble phosphorylated glucan with cyclophosphamide was able to prevent the characteristic development of leukopenia following cyclophosphamide adminstration. This should maintain resistance to infectious diseases in the presence of toxic chemotherapeutic agents while exerting a synergistic effect on tumor regression, as demonstrated in Section 7.8., supra.

7.10. DIRECT CYTOSTATIC EFFECTS ON NEOPLASTIC CELLS

7.10.1. CYTOSTATIC EFFECT ON PROLIFERATION OF LYMPHOCYTIC LEUKEMIC CELLS IN VITRO

This series of experiments demonstrates the ability of soluble phosphorylated glucan to inhibit the proliferation rate of murine lymphocytic leukemic cells in vitro.

L-1210 lymphocytic leukemic cells, maintained in culture, were plated in microtiter wells at a concentration of $2\times10^5$ cells/wel.. Soluble phopsphorylated glucan (500 ug/well) or particulate glucan (100 ug/well) was added and the cells incubated for a period of 24 hours. An equal volume of culture medium (RPMI-1640 supplemented with 7.5% Fetal Calf serum) was added to the control cultures. $^3$H-thymidine (0.5 u Ci/well) was added to all cultures and incubations were continued for another period of 24 hours. Cell proliferation was evaluated by determining the incorporaton of $^3$H-thymidine. Results are illustrated in Table 14.

TABLE 14
COMPARATIVE EFFECT OF SOLUBLE PHOSPHORYLATED GLUCAN AND PARTICULATE GLUCAN ON THE IN VITRO PROLIFERATION OF MURINE LYMPHOCYTIC LEUKEMIA CELLS

| Treatment Group[a] | $^3$H—Thymidine Uptake (cpm) | % Inhibition of Cell Proliferation |
|---|---|---|
| Control | 3547 ± 310 | 0 |
| Soluble Phosphorylated Glucan | 407 ± 38 | 88.5 ± 9.3 |
| Particulate Glucan | 2269 ± 293 | 36.0 ± 4.6 |

[a]L-1210 cells ($2 \times 10^5$/well) were incubated in the presence of soluble phosphorylated glucan (0.5 mg/well) or particulate glucan (0.1 mg/well) for 24 hours. $^3$H—thymidine (0.5 uCi/well) was added to measure tumor cell proliferation. N = 24 wells/group.

As shown in Table 14, particulate glucan inhibited tumor cell proliferation 36%. In marked contrast, soluble phosphorylated glucan inhibited tumor cell proliferation about 88.5%. Thus, one of the mechanisms by which soluble phosphorylated glucan may inhibit tumor growth and metastases is by its ability, in as yet an undefined manner, to directly inhibit tumor cell proliferation.

7.10.2. CYTOSTATIC EFFECT ON PROLIFERATION OF SARCOMA AND MELANOMA TUMOR CELLS IN VITRO

Another series was conducted to evaluate the direct effect of soluble phosphorylated glucan on normal and tumor cell lines in vitro.

Sarcoma M5076, melanoma B16 and adenocarcinoma BW10232 were harvested from in vitro cultures. The tumor cells were dispersed by gentle shaking and then centrifuged for 10 minutes at $100\times g$. The cell pellet was washed twice and resuspended at a final concentration of $5\times10^6$ cells/ml of culture medium (RPMI 1640 supplemented with 10% heat-inactivated fetal calf serum).

Normal cells were obtained by aseptic excision of spleens of C57BL/6J mice. The spleens were minced in a sterile petri dish containing RMPI 1640. Prior to centrifugation for 10 minutes at 100 $\times$g, the spleen homogenate was passed through a 22 mesh steel screen to remove connective tissue debris. Erythrocytes were removed from the spleen preparation by hypotonic lysss. The cell pellet was washed twice and resuspended in RPMI 1640 at a final concentration of $5\times10^6$ cells/ml.

Normal bone marrow cells were obtained by excising femurs of C57BL/6J mice and flushing the marrow cavities with 6 ml of RPMl 1640 medium. The bone marrow cell suspension was collected, washed twice, centrifuged and diluted to a concentratin of $5\times10^6$ cells/ml Normal thymocytes were obtained from C57BL/6J mice (6-8 weeks old). The thymus was aseptically removed and dispersed in a glass tissue grinder. The thymocytes were centrifuged and washed twice in RMPI 1640. The cell pellet was resuspended at a final concentration of $5 \times 10^6$ cells/ml An aliquot of normal or tumor cells ($5 \times 10^5$ cells) was added to Corning microtiter plates in culture medium (100 ul) containing 1, 10 or 100 ug of soluble phosphorylated glucan/well. An equal aliquot of normal or tumor cells was added to an equal volume of culture medium. The plates were incubated for 40 hours at 37° C. under 5% $CO_2$. $^3$H-thymidine (0.3 uCi/well) (New England Nuclear, 6.7 Ci/mmole) was added to all cultures. The cultures were incubated an additional 8 hours, centrifuged ($200 \times g$) and then washed three times with RPMI 1640. Two hundred microliters of distilled water was added to each well, and the samples were freeze-thawed twice. Cell proliferation was evaluated by determining the incorporation of $^3$H-thymidine. Results are illustrated in Table 15.

TABLE 15

DIRECT EFFECT OF SOLUBLE PHOSPHORYLATED GLUCAN (SPGLN) ON 3H—THYMIDINE UPTAKE BY NORMAL AND TUMOR CELL LINES IN VITRO[a]

| Cells | $^3$H—Thymidine Uptake (CPM $\times 10^2$) Concentration SPGLN (ug/well) | | | |
|---|---|---|---|---|
| | 0 | 1 | 10 | 100 |
| Normal Cells | | | | |
| Bone marrow | 10.7±1.6 | 13.6±1.1 | 15.7±1.1* | 11.0±1.0 |
| Splenocytes | 5.4±0.9 | 10.9±1.0# | 8.0±0.7* | 6.7±0.6 |
| Thymocytes | 5.2±0.5 | 4.8±0.5 | 5.2±0.5 | 6.6±0.6 |
| Tumor Cells | | | | |
| Sarcoma M5076 | 23.7±2.0 | 15.5±0.9** | 17.3±0.1 | 13.7±0.8# |
| Adenocarcinoma BW10232 | 14.4±0.2 | 12.1±0.5 | 10.5±0.6 | 13.7±1.3 |
| Melanoma B16 | 27.5±3.8 | 8.4±0.5# | 8.4±1.1# | 4.0±0.5# |

[a]Cells ($5 \times 10^5$/well) were incubated with soluble phosphorylated glucan for 40 hours. 3H—thymidine (0.3 uCi/well) was added to measure cell proliferation. Values are expressed as mean ± standard error. Statistical comparisons were made relative to the control values (i.e., 0 ug/well SPGLN) N = 8–16/group.
*p < 0.05.
**p < 0.01.
p < 0.001.

As demonstrated in Table 15, soluble phosphorylated glucan at 1, 10 and 100 ug/well significantly inhibited proliferation of sarcoma M5076 cells, i.e, 35% (p<0.01), 27% (p<0.05) and 42% (p<0.001) respectively. Moreover, soluble phosphorylated glucan at 1, 10 and 100 ug/well very highly significantly (p<0.001) inhibited proliferation of melanoma B16 cells, i.e., 69%, 69 and 85% respectively. On the other hand, soluble phosphorylated glucan had no significant effect on proliferation of adenocarcinoma BW10232 cells in vitro.

In marked contrast, soluble phosphorylated glucan at 10 ug/well, and at 1 and 10 ug/well enhanced proliferation of normal bone marrow cells (47%; p<0.05) and of normal splenocytes [(101%; p<0.001) and 48%; p<0.05)] respectively. No significant effect on normal thymocyte proliferation was noted.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A pharmaceutical composition for the treatment of a malignant neoplastic disease in animals or humans, comprising a therapeutically effective amount of a soluble glucan which comprises a phosphorylated poly-[beta-(1-3)glucopyranose] chain which is characterized by:
   (a) the capability of dissolving in water or an aqueous solution;
   (b) being non-toxic, non-immunogenic and substantially non-pyrogenic; and
   (c) the capability of exerting a profound immunobiological response when administered in vivo to an animal or to a human,
and a physiologically acceptable carrier.

2. The composition according to claim 1, in which the soluble glucan is further characterized by the substantially complete absence of triple helical chains as determined by nuclear magnetic resonance spectroscopy.

3. The composition according to claim 1, in which the soluble glucan is further characterized by having a degree of phosphorylation ranging from about 1.4% to about 3.4%.

4. The composition according to claim 1, in which the soluble glucan is further characterized by having a molecular weight ranging from about 10,000 to about 100,000 daltons.

5. The composition according to claim 1, in which the soluble glucan ss further characterized by having a molecular weight ranging from about 100,000 to about 500,000 daltons.

6. The composition according to claim 1, in which the soluble glucan is obtained from a microbial source.

7. The composition according to claim 6, in which the microbial source is Saccahromyces cerevisiae.

8. The soluble glucan according to claim 6, in which the microbial source is Coriolus versicolor.

9. The soluble glucan according to claim 6, in which the microbial source is Sclerotium glucanium.

10. The composition according to claim 1, further comprising an anti-tumor agent.

11. The composition according to claim 10, in which the anti-tumor agent is cyclophosphamide.

12. A method for treatment of a malignant neoplastic disease in animals and humans, comprising administering to an animal or a human so affected a therapeutically effective amount of a soluble glucan which comprises a phosphorylated poly-[beta-(1-3)glucopyranose] chain which is characterized by:
   (a) the capability of dissolving in water or an aqueous solution;
   (b) being non-toxic, non-immunogenic and substantially non-pyrogenic; and
   (c) the capability of exerting a profound immunobiological response when administered in vivo to an animal or to a human.

13. A method for treatment of a malignant neoplastic disease in animals and humans, comprising administering to an animal or a human so affected a therapeutically effective amount of the copposition according to claim 1.

14. A method for treatment of a malignant neoplastic disease in animals and humans, comprising administering to an animal or a human so affected a therapeutically effective amount of the composition according to claim 10.

15. The method according to claim 14, in which the anti-tumor agent is cyclosphosphamide.

16. The method according to claim 12, in which the soluble phosphorylated glucan is administered topically, intravenously, intraperitoneally, subcutaneously, orally or by inhalation.

17. The method according to claim 13, in which the composition is administered topically, intravenously, intraperitoneally, subcutaneously, orally or by inhalation.

18. The method according to claim 14, in which the soluble phosphorylated glucan is administered topically, intravenously, intraperitoneally, subcutaneously, orally, or by inhalation.

* * * * *